US010416427B2

(12) United States Patent
Brown et al.

(10) Patent No.: US 10,416,427 B2
(45) Date of Patent: Sep. 17, 2019

(54) SCAN-BASED IMAGING WITH VARIABLE SCAN SPEED USING PREDICTIONS OF REGION-OF-INTEREST POSITIONS

(71) Applicant: INSTITUT NATIONAL D'OPTIQUE, Québec (CA)

(72) Inventors: Rob Brown, Québec (CA); Jean-Pierre Bouchard, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 0 days.

(21) Appl. No.: 15/904,033

(22) Filed: Feb. 23, 2018

(65) Prior Publication Data
US 2018/0246309 A1 Aug. 30, 2018

Related U.S. Application Data

(60) Provisional application No. 62/463,056, filed on Feb. 24, 2017.

(51) Int. Cl.
*H04N 1/04* (2006.01)
*G02B 21/00* (2006.01)
(Continued)

(52) U.S. Cl.
CPC ..... *G02B 21/0072* (2013.01); *G02B 21/0032* (2013.01); *G02B 21/0076* (2013.01); *G02B 21/0084* (2013.01); *G02B 21/06* (2013.01); *H04N 1/047* (2013.01); *H04N 1/0411* (2013.01); *H04N 1/0443* (2013.01);
(Continued)

(58) Field of Classification Search
CPC ...... H04N 1/17; H04N 1/0411; H04N 1/0443; H04N 1/047; H04N 1/0476; H04N 1/053
See application file for complete search history.

(56) References Cited

U.S. PATENT DOCUMENTS 3,609,225 A * 9/1971 Stallard .................... H04N 1/17
358/1.9
3,627,921 A * 12/1971 Weller ..................... H04N 1/17
358/474
(Continued)

FOREIGN PATENT DOCUMENTS

GB  1159402 A * 7/1969 ........... H04N 1/0057

OTHER PUBLICATIONS

Lillis, K.P. et al., Two-photon imaging of spatially extended neuronal network dynamics with high temporal resolution, J Neurosci Methods, 172(2): 178-184, Jul. 2008.

*Primary Examiner* — Ted W Barnes
(74) *Attorney, Agent, or Firm* — Maschoff Brennan

(57) ABSTRACT

A method and system for obtaining an image of object, for example an optical section of a sample, are disclosed. The image includes a plurality of scan lines to be acquired. The method includes, for a current one of the scan lines to be acquired, a step of determining positions of one or more predicted regions of interest along the current scan line based on at least one previously acquired predictive scan line. The method also includes a step of acquiring the current scan line along a scan path in accordance with a variable scan speed profile including at least one slower speed component along segments of the scan path corresponding to the positions of the one or more predicted regions of interest and at least one faster speed component elsewhere along the scan path.

24 Claims, 15 Drawing Sheets

(51) Int. Cl.
  *H04N 1/17* (2006.01)
  *H04N 1/047* (2006.01)
  *G02B 21/06* (2006.01)
  *G01N 21/64* (2006.01)

(52) U.S. Cl.
  CPC ............ *H04N 1/0476* (2013.01); *H04N 1/17* (2013.01); *G01N 21/6458* (2013.01); *G01N 2021/6439* (2013.01); *G02B 21/006* (2013.01)

(56) References Cited

U.S. PATENT DOCUMENTS

| | | | | |
|---|---|---|---|---|
| 3,632,867 A * | 1/1972 | Markow | ................... | H04N 1/17 358/409 |
| 3,643,016 A * | 2/1972 | Dattilo | ................... | H04N 1/17 358/438 |
| 3,646,255 A * | 2/1972 | Markow | ................... | H04N 1/17 358/486 |
| 3,646,256 A * | 2/1972 | Jacob | ................... | H04N 1/17 358/1.9 |
| 3,670,099 A * | 6/1972 | Oliver | ................... | H04N 1/17 358/486 |
| 3,912,861 A * | 10/1975 | Vandling | ................... | H04N 1/17 358/475 |
| 3,919,464 A * | 11/1975 | Kondoh | ................... | H04N 1/17 348/197 |
| 3,955,045 A * | 5/1976 | Ford, Jr. | ................... | H04N 1/17 358/484 |
| 4,228,469 A * | 10/1980 | Ford, Jr. | ................... | H04N 1/00095 358/486 |
| 5,568,270 A * | 10/1996 | Endo | ................... | H04N 1/17 358/474 |
| 5,684,601 A * | 11/1997 | Endo | ................... | H04N 1/17 358/444 |
| 5,719,970 A * | 2/1998 | Aoki | ................... | H04N 1/047 358/473 |
| 6,438,201 B1 | 8/2002 | Mazess et al. | | |
| 7,941,286 B2 * | 5/2011 | Proksch | ................... | G01Q 10/06 702/127 |

* cited by examiner

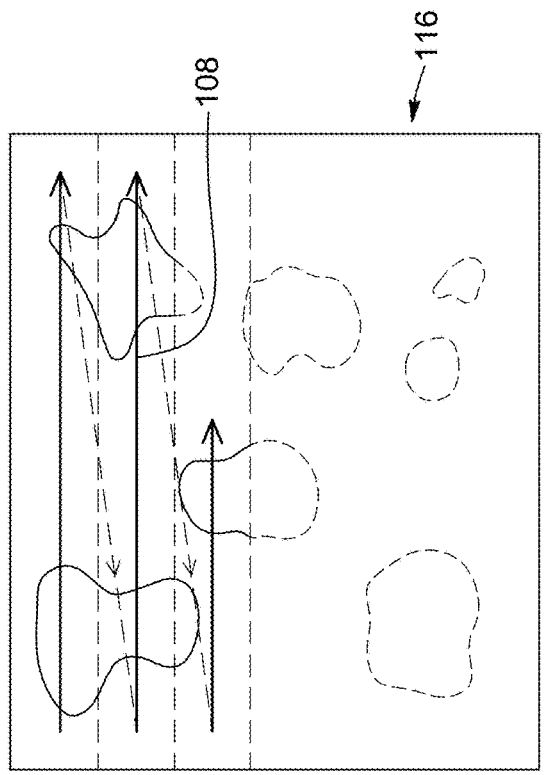
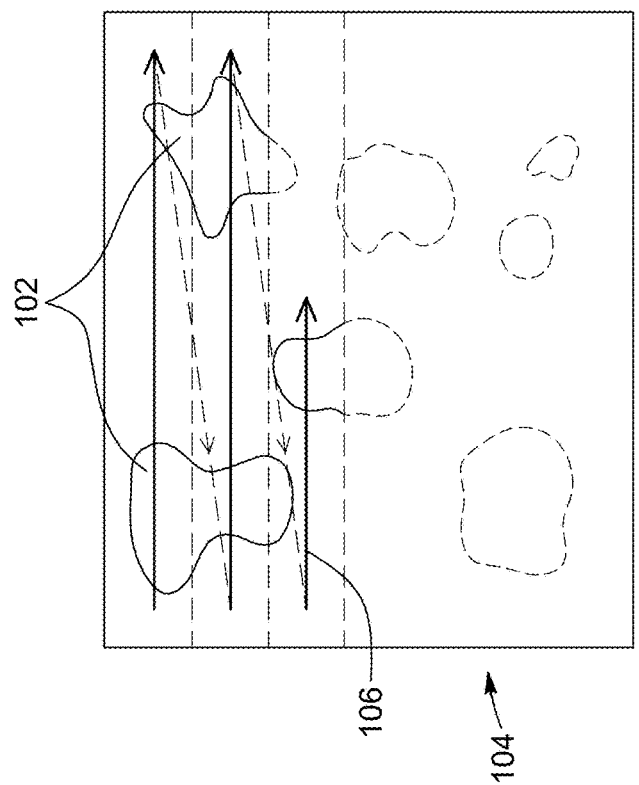

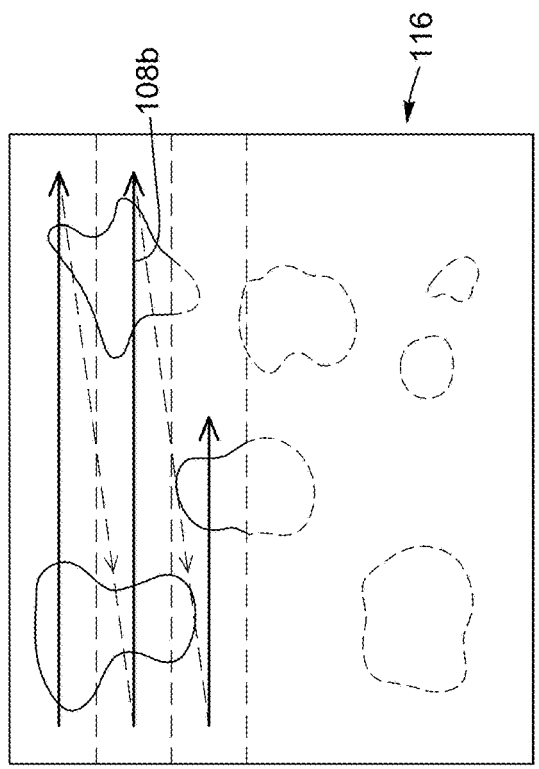
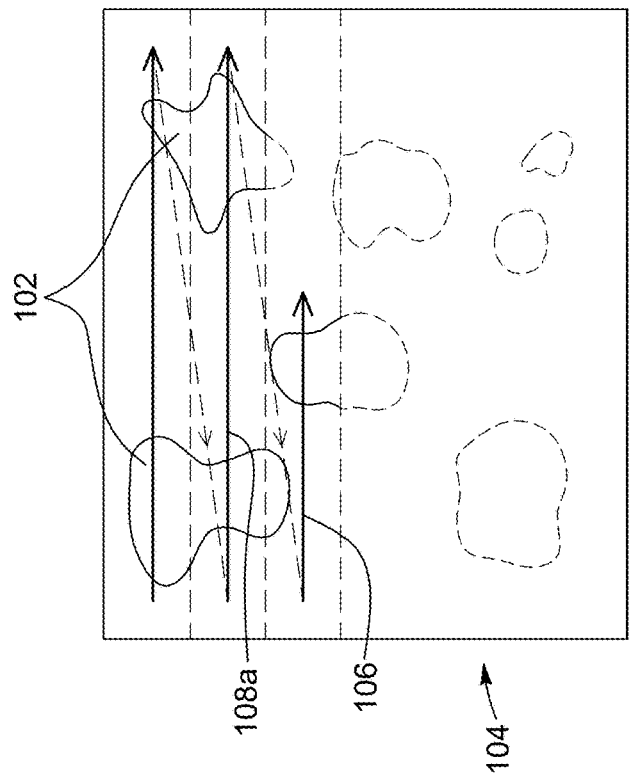
FIG. 11B
FIG. 11A

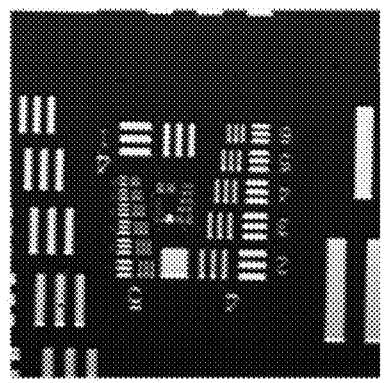
FIG. 15A
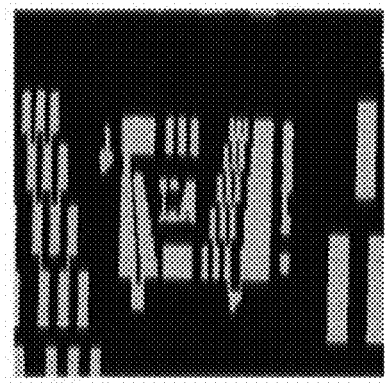
FIG. 15B
FIG. 15C
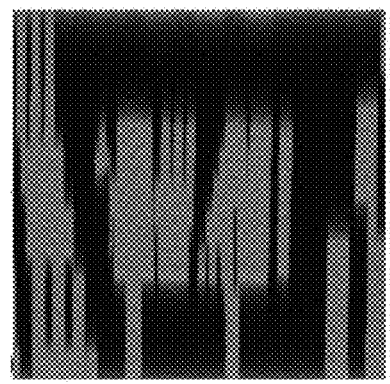
FIG. 15D

SCAN-BASED IMAGING WITH VARIABLE SCAN SPEED USING PREDICTIONS OF REGION-OF-INTEREST POSITIONS

RELATED PATENT APPLICATION

The present application claims priority from U.S. Provisional Patent Application No. 62/463,056 filed on Feb. 24, 2017, the disclosure of which is incorporated herein by reference in its entirety.

TECHNICAL FIELD

The technical field generally relates to imaging techniques, and more particularly, to techniques for increasing scan speed in point-based scan imaging, for example in confocal microscopy.

BACKGROUND

Single-beam scanning using galvanometers is common in several fields including cellular microscopy. Single-beam scanning-based imaging techniques are relatively slow because the image pixels are acquired sequentially through the raster scanning of a single imaging point. This can be particularly detrimental in the field of high-content screening involving the confocal scanning of thousands of high-resolution cellular images in an automated fashion. In these high-content screening experiments, image acquisition times for a single frame may be of the order of tens of seconds in cases where there are limitations on the signal collected from the sample, as is the case in time-domain fluorescence-lifetime imaging microscopy (FLIM). These screens can involve hundreds of differently treated cellular samples, for example in a 384-well plate, for which multiple images must be taken of different sites within each condition to achieve statistically relevant data. The resulting need for thousands of images translates to multiple hours of imaging. This can for example be an issue in applications where the interaction to be measured is transient, where the sample is not stable, or where a time-course is desired to follow the impacts of the experimental treatment. Similar issues may be encountered in other "photon-starved" optical imaging techniques.

Efforts to improve scan speeds have concentrated on higher speed scanning mechanisms (e.g., rotating mirrors, resonant galvanometers) and multiconfocal (e.g., spinning disk) approaches. However, these approaches generally have drawbacks in terms of reduced spatial resolution and lower signal-to-noise ratios. Furthermore, in situations where the signal is limited by saturation or photobleaching of the analytes with excitation light, further reduction in imaging time is not possible or practical using a faster scan speed. In these cases, the scanning speed is limited not by the speed of the scanning mechanism, but by the rate of photons that can be collected from the illuminated sample region. Conventional methods for improving scanning speed while preserving image quality generally involve one or more of the following: increasing the energy of the collected signal by enlarging the numerical aperture of the collecting optics; improving the throughput of the collection optics; and increasing the quantum efficiency of the detector. The development of techniques for increasing or improving these parameters has been a topic of research for decades, and although improvements have been made, in some cases they are approaching physical limitations.

Another known approach, aimed at increasing the speed of neuron scanning to make time resolved images, is disclosed in Lillis et al. "Two-photon imaging of spatially extended neuronal network dynamics with high temporal resolution", *Journal of Neuroscience Methods*, volume 172, issue 2, pages 178-184 (2008). In an experiment disclosed in this reference, a pre-image is acquired, and a vector-based scan route is determined to maximize cellular analysis against intercellular spaces. In the intercellular spaces the scanning speed was increased using a maximum acceleration, maximum deceleration approach. This path was then used for repeated imaging of the same sample for rapid updates in a time-course imaging set. This approach is not suitable for high-content screening, however, since it requires a full raster scan image to plan the optimal galvanometric scan pattern for each field of view. A separate high-speed full-field imaging system could be incorporated for this purpose, but has the drawbacks of adding to system cost and complexity, and potentially resulting in photobleaching of some fluorophores prior to imaging.

Challenges therefore remain in the development of scanning imaging techniques that can alleviate at least some of the above-mentioned drawbacks.

SUMMARY

The present description generally relates to scanning imaging techniques that can predict positions of upcoming regions of interest in an image of an object, for example a sample or a target region. In some implementations, the present techniques provide methods and systems for determining regions of interest in an image in line with the image acquisition process to perform more efficient scanning of objects.

In accordance with an aspect, there is provided a method for obtaining an image of an object, the image including a plurality of scan lines to be acquired. The method includes, for a current one of the scan lines to be acquired:

determining positions of one or more predicted regions of interest along the current scan line based on at least one previously acquired predictive scan line; and acquiring the current scan line along a scan path in accordance with a variable scan speed profile including at least one slower speed component along segments of the scan path corresponding to the positions of the one or more predicted regions of interest and at least one faster speed component along other segments of the scan path.

In some implementations, the at least one previously acquired predictive scan line includes at least one of the scan lines of the image to be acquired, such as the scan line acquired immediately before the current scan line, for example, or multiple scan lines acquired successively before the current scan line. In other implementations, the at least one previously acquired predictive scan line need not be one of the scan lines of the image containing the current scan line. For example, in some scenarios, the at least one previously acquired predictive scan line may be a flyback scan line acquired between the current scan line and the scan line of the image acquired immediately before the current scan line.

In some implementations, the at least one previously acquired predictive scan line can belong to one or more other images, different from the image containing the current scan line. In one scenario, the image containing the current scan line and the one or more images containing the at least one previously acquired predictive scan line can be acquired using distinct detection channels and either single or multiple illumination sources. Depending on the application, the image containing the current scan line and the one or more images containing the at least one previously acquired predictive scan line can be acquired simultaneously, concurrently, sequentially, in an interleaved manner, or using other acquisition schemes.

In some implementations, the at least one previously acquired predictive scan line can include multiple spatially registered predictive scan lines acquired using multiple detection channels, one of which possibly, but not necessarily, belongs to the image containing the current scan line. In such implementations, the step of determining the positions of the one or more predicted regions of interest along the current scan line can include identifying a potential region of interest as one of the one or more predicted regions of interest if a specified condition is met for at least one of the multiple spatially registered predictive scan lines. That is, depending on the application, a single, some or all the predictive scan lines may be required to meet a specified condition for a potential region of interest to be considered as a predicted region of interest.

In some implementations, the step of determining the positions of the one or more predicted regions of interest can include the following steps:
receiving each previously acquired predictive scan line as a series of pixel values as a function of position along the previously acquired predictive scan line;
comparing, for each previously acquired predictive scan line, the pixel values against one or more threshold criteria; and
identifying the positions of the one or more predicted regions of interest of the current scan line based on or as the positions of those pixel values that meet the one or more threshold criteria.

In some implementations, the one or more threshold criteria include at least one of a presence-absence threshold criterion that the pixel values exceed a presence intensity threshold and a saturation threshold criterion that the pixel values remain below a saturation intensity threshold.

In some implementations the step of determining the positions of the one or more predicted regions of interest further includes, prior to receiving each previously acquired predictive scan line, acquiring each previously acquired predictive scan line.

In some implementations, the step of acquiring the current scan line can include the following steps:
scanning an illumination beam over a portion or strip of the object corresponding to the current scan line in accordance with the variable scan speed profile;
detecting an object signal (e.g., a light signal) emanating from the scanned portion or strip of the object; and
generating the current scan line from the detected object signal.

In some implementations, the step of acquiring the current scan line can include a preliminary step of establishing the variable scan speed profile based on the identified positions of the one or more predicted regions of interest.

In some implementations, the at least one slower speed component can consist of a single slower speed component with a slower nominal speed, and the at least one faster speed component can consist of a single faster speed component with a faster nominal speed. For example, in some implementations, a ratio of the faster nominal speed to the slower nominal speed can range between two and ten.

In some implementations, there is provided a method for imaging an optical section of a sample using single-point scan imaging microscopy or the like, the image being defined by a plurality of scan lines to be acquired line by line in a raster scan. The method includes, for each of the scan lines:
determining a predicted position of one or more regions of interest along a path of the scan line based on at least one previously acquired proximal scan line; and
acquiring said scan line through a scan of the sample at a variable speed including at least one slower speed component along the predicted positions of the one or more regions of interest and at least one faster speed component along other positions.

In accordance with another aspect, there is provided a method of performing a scan for acquiring a scan line of an image of an object. The method includes:
initiating the scan at a scan speed;
monitoring an absence or an end of a region of interest for upcoming pixels of the scan line based on absence-predictive variations in image signal intensity and, upon detection of said absence or end, setting the scan speed to a faster scan speed value;
monitoring an onset of a region of interest for upcoming pixels of the scan line based on onset-predictive variations in image signal intensity and, upon detection of said onset, setting the scan speed to a slower scan speed value; and
repeating the monitoring steps until the end of the scan line is reached.

In accordance with another aspect, there is provided a non-transitory computer readable storage medium storing computer executable instructions thereon for determining a variable scan speed profile of a scan for acquiring a current scan line of an image of an object, the computer executable instructions, when executed by a processor, cause the processor to perform the following steps:
receiving at least one previously acquired predictive scan line, each of which provided as a series of pixel values as a function of position along the previously acquired predictive scan line;
determining positions of one or more predicted regions of interest along the current scan line based on the pixel values of the at least one previously acquired predictive scan line; and
determining the variable scan speed profile from the determined positions of the one or more predicted regions of interest, the variable scan speed profile including at least one slower speed component along segments of the scan corresponding to the positions of the one or more predicted regions of interest and at least one faster speed component along other segments of the scan.

In some implementations, the step of determining the positions of the one or more predicted regions of interest includes:
comparing, for each previously acquired predictive scan line, the pixel values against one or more threshold criteria; and
identifying the positions of the one or more predicted regions of interest of the current scan line based on the positions of those pixel values that fulfill the one or more threshold criteria.

In some implementations, the one or more threshold criteria include at least one of a presence-absence threshold criterion that the pixel values exceed a presence intensity threshold and a saturation threshold criterion that the pixel values remain below a saturation intensity threshold.

In some implementations, the at least one previously acquired predictive scan line can include multiple spatially registered predictive scan lines acquired using multiple detection channels, one of the predictive scan lines belonging to the image containing the current scan line. In such implementations, the step of determining the positions of the one or more predicted regions of interest along the current scan line can include identifying a potential region of interest as one of the one or more predicted regions of interest if a specified condition is met for at least one of the multiple spatially registered predictive scan lines.

In some implementations, the computer executable instructions further cause the processor to control a scanner assembly to scan, in accordance with the variable scan speed profile, an illumination beam along a portion or strip of the object corresponding to the current scan line.

In accordance with another aspect, there is provided an imaging system for obtaining an image of an object, for example the optical section of a sample, the image including a plurality of scan lines to be acquired, the imaging system including:
- an illumination assembly generating an illumination beam;
- a scanner assembly scanning the illumination beam along a scan path across a portion of the object;
- a detector assembly detecting an object signal emanating from the scanned portion of the object and generating, from the detected object signal, a current one of the scan lines; and
- a processor configured to determine positions of one or more predicted regions of interest along the current scan line based on at least one previously acquired predictive scan line, and to control the scanner assembly to scan the illumination beam over the portion of the object corresponding to the current scan line in accordance with a variable scan speed profile including at least one slower speed component along segments of the scan path corresponding to the positions of the one or more predicted regions of interest and at least one faster speed component along other segments of the scan path.

In some implementations, the processor can include a dedicated processor, for example a field-programmable gate array.

In some implementations, the imaging system can use confocal microscopy and, more particularly, confocal laser scanning microscopy.

In some implementations, the detected object signal can be an optical signal, although other types of signals, for example acoustic, can also be detected in other implementations.

In some implementations, the imaging system may be embodied functionally as a single-beam scan-based imaging system configured to perform the following steps: raster-scanning a sample with probing light; detecting energy (optical, acoustic or otherwise) emanating from the sample as a result of this probing; generating image data from the detected energy; providing the image data to a dedicated processor for comparison against threshold criteria; calculating a fast-axis scan speed profile for the next scan line to determine which portions of the next scan line are to be acquired at a faster scan speed and which ones are to be acquired at a slower scan speed; and supplying the fast-axis scan speed profile to a scanner assembly of the imaging system to acquire the next scan line, such that regions of the next scan line which are not of interest will be scanned at a faster scan rate than regions of interest, with a view of decreasing the overall duration of the scanning session.

In some implementations, the present techniques provide methods and/or devices having an increased scan speed in raster scans of images of sparse objects, without significantly sacrificing the image quality of these objects. To this end, scan speed is increased during portions of the raster scan where no or very few objects of interest are expected to be present as predicted by one or more proximal scanned regions which have previously been acquired within the same scan. Scan speed is kept at a lower value for image acquisition in regions which are expected to contain objects of interest. In some implementations, predictions of regions and objects of interest are assessed by applying either a threshold value or an algorithm to detector output values recorded from proximal regions which have already been scanned.

In some implementations, the present techniques can take advantage of the absence or scarcity of useful or relevant information outside of specific regions of interest of a sample. By way of example, for cell-based screenings, the coverage of the imaging surface is often well below 50%, as cells are seeded randomly on the image surface to a level below confluence to ensure that cells do not stack up on one another. Some embodiments disclosed herein employ a strategy of improving scanning speed without sacrificing image resolution or signal-to-noise ratio, by improving scanning efficiency. This can ensure, or help ensure, that the available measurement time is spent predominantly on information-rich regions of the image without requiring a priori knowledge or information about the positions of these regions of interest. Thus, by performing a faster scan over regions where no or only a few cells are present, such embodiments have the potential to significantly reduce scanning time in high-content screening imaging sessions.

It is to be noted that other method steps may be performed prior, during or after the above-described steps. The order of one or more of the steps may also differ, and some of the steps may be omitted, repeated and/or combined, depending on the application. It is also to be noted that some method steps can be performed using various image processing techniques, which can be implemented in hardware, software, firmware or any combination thereof.

Other features and advantages of the present description will become more apparent upon reading the following non-restrictive description of specific embodiments thereof, given by way of example only, with reference to the appended drawings. Although specific features described in the above summary and in the detailed description below may be described with respect to specific embodiments or aspects, it should be noted that these specific features can be combined with one another, unless stated otherwise.

BRIEF DESCRIPTION OF THE DRAWINGS

FIG. 4 also provides a schematic representation of an image of the optical section, where the image can be acquired using the techniques disclosed herein.

FIGS. 9A and 9B are schematic representations of the acquisition of a current scan line of an image (FIG. 9A) of an optical section, in accordance with a possible embodiment, wherein the at least one predictive scan line associated with the current scan line belongs to another image (FIG. 9B), acquired using another detection channel but the same illumination source as the image containing the current scan line.

FIGS. 11A and 11B are schematic representations of an embodiment in which multiple spatially registered predictive scan lines (FIGS. 11A and 11B) are used to predict the locations of regions of interest of a current scan line of an image (FIG. 11A).

FIGS. 15A and 15B are two images of a same sample acquired in accordance with two possible embodiments. FIGS. 15C and 15D are the scan speed maps used to acquire the images in FIGS. 15A and 15B, respectively,

DETAILED DESCRIPTION

Figure 1A:
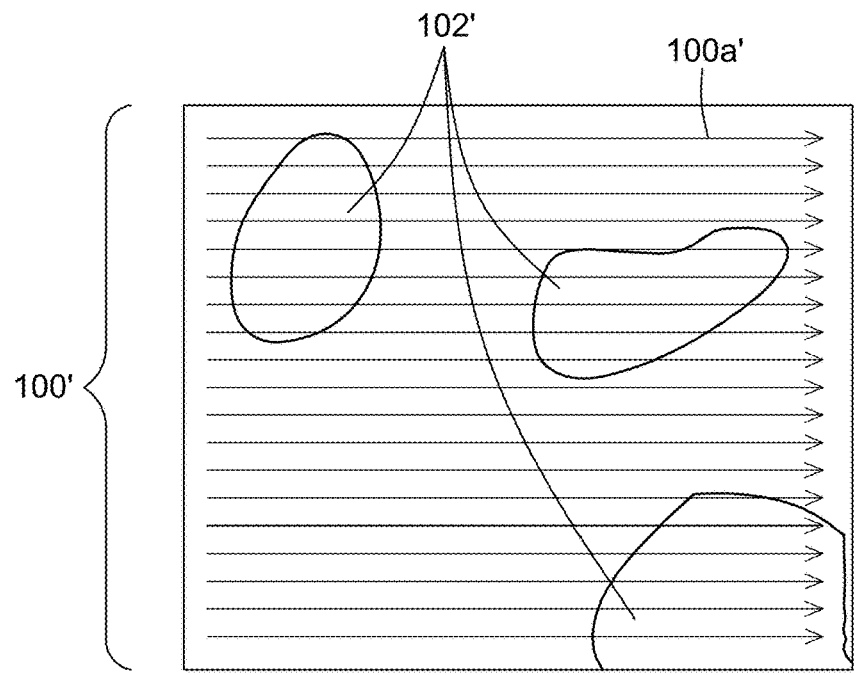
FIG. 1A (PRIOR ART) is a schematic representation of a typical conventional raster scan measurement to obtain an image of a sample, where all the scan lines are acquired at the same scan speed.

In the present description, similar features in the drawings have been given similar reference numerals. To avoid cluttering certain figures, some elements may not be indicated, if they were already identified in a preceding figure. It should also be understood that the elements of the drawings are not necessarily depicted to scale, since emphasis is placed on clearly illustrating the elements and structures of the present embodiments. Furthermore, positional descriptors indicating the location and/or orientation of one element with respect to another element are used herein for ease and clarity of description. Unless otherwise indicated, these positional descriptors should be taken in the context of the figures and should not be considered limiting. More particularly, it will be understood that such spatially relative terms are intended to encompass different orientations in the use or operation of the present embodiments, in addition to the orientations exemplified in the figures.

Unless stated otherwise, the terms "connected" and "coupled", and derivatives and variants thereof, refer herein to any connection or coupling, either direct or indirect, between two or more elements. For example, the connection or coupling between the elements may be mechanical, optical, electrical, magnetic, logical, or a combination thereof.

The terms "a", "an" and "one" are defined herein to mean "at least one", that is, these terms do not exclude a plural number of items, unless stated otherwise. It should also be noted that terms such as "substantially", "generally" and "about", that modify a value, condition or characteristic of a feature of an exemplary embodiment, should be understood to mean that the value, condition or characteristic is defined within tolerances that are acceptable for the proper operation of this exemplary embodiment for its intended application.

The terms "light" and "optical" are used to refer herein to radiation in any appropriate region of the electromagnetic spectrum. More particularly, these terms are not limited to visible light, but can also include invisible regions of the electromagnetic spectrum including, without limitation, the terahertz (THz), infrared (IR) and ultraviolet (UV) spectral bands. For example, in non-limiting embodiments, the imaging systems that can implement the present techniques can be sensitive to light having a wavelength band lying somewhere in the range from about 400 to about 780 nanometers (nm). Those skilled in the art will understand, however, that this wavelength range is provided for illustrative purposes only and that the present techniques may operate beyond this range.

The present description generally concerns the imaging of an object, such as a sample or a target, using scan-based imaging techniques, for example point scanning imaging, in applications such as microscopy and remote sensing.

In the present description, the term "point scanning microscopy" is intended to encompass various imaging techniques in which an object or sample is scanned by illumination light, and an image of the sample is acquired by detecting an optical, acoustic or other response from the scanned sample. The detected optical response from the sample can include, without limitation, light emanating from the sample due to transmission, reflection, refraction, scattering, fluorescence and emission processes, absorption, and/or nonlinear optical phenomena. In point scanning microscopy, as only one point of the sample is illuminated at a time, two-dimensional (2D) imaging involves a raster scan of the sample, such that the image is made up of a plurality of parallel scan lines, each scan line imaging a respective strip-shaped area of the sample. It will be understood that the term "scan line" or "line" is used herein as commonly used in the art, that is, as a shorthand for describing the image data acquired over one linear scan over the sample. Each scan line is typically made up of a series of pixel data or pixels representing linearly consecutive portions of a strip-shaped area of the sample.

In the present description, the term "laser scanning microscopy" refers to optical microscopy techniques where laser radiation is used for sample illumination. Non-limiting examples of scanning imaging modalities in which embodiments of the present techniques may be implemented or applied include: confocal microscopy; multiphoton microscopy, for example two-photon microscopy; fluorescence-lifetime imaging microscopy (FLIM); second-harmonic imaging or third-harmonic imaging microscopy; reflectance microscopy; coherent anti-Stokes Raman scattering (CARS) microscopy; stimulated Raman scattering microscopy; sum-frequency generation microscopy; and hyperspectral microscopy.

Some embodiments disclosed herein may be of interest for applications in confocal microscopy, including confocal laser scanning microscopy (CLSM) where laser radiation is used to illuminate the sample. Confocal microscopy involves the use of one or more spatial pinholes in the optical path to eliminate out-of-focus light rays, and therefore relies on the detection of sometimes very weak signals, requiring a very long imaging process to obtain a result with a high signal-to-noise ratio. As mentioned above, high-content screening measurements involving confocal scanning can be useful for high-resolution cellular imaging, for example in drug development applications.

However, the present techniques are not limited to confocal microscopy for cellular imaging, or to other types of microscopy dependent on speed and/or throughput, such as high-content screening microscopy. Other non-limiting examples of possible applications include other microscopy techniques, remoting sensing and lidar, time-course imaging for moving objects and samples, medical imaging, three-dimensional (3D) sensing device (e.g., for fine detection of the size and/or shape of objects), and part inspection on conveyor-belt-type part inspection with line-based scanning where the orientation and location of parts are not known in advance. Furthermore, any object that can be imaged with single-point scan imaging may a priori benefit from the present techniques. In some embodiments, the sample can be a biological specimen (e.g., cells, organoids, spheroids, tissues, organs, blood vessels, and the like), although various other types of objects, targets, media, materials, and features of interest can be imaged, in other embodiments.

In some implementations, the techniques disclosed herein rely on the use of automated region of interest (ROI) definition, by measuring the detected intensity from zones proximal to the zone to be scanned, and inferring, from this measurement, the presence and location of ROIs in the zone to be scanned while in the process of performing a single scan. Since adjacent raster scan lines generally have similar intensity profiles for objects significantly larger than the pixel size, the determined ROI locations in a previously acquired scan line can be used to predict the ROI locations in a scan line to be acquired. This prediction can be used to tailor or adjust the scan speed along the scan line to be acquired so that the scan speed is relatively slower over the predicted ROIs, to achieve an acceptable signal-to-noise ratio, and relatively faster between ROIs, where lower resolution can be tolerated without adversely compromising image quality. For example, some embodiments can use a variable scan speed profile that alternates between a slower speed value and a faster speed value depending on whether an ROI is predicted to be present (slower speed value) or absent (faster speed value) at a given position along the scan line.

Depending on the application, the faster speed value can be limited by various factors including, but not limited to, the highest stable scan speed achievable by the scanning mechanism (e.g., a scan speed corresponding to a scan line acquisition rate of one millisecond per scan line or better, for many high-performance galvanometer systems); the acceleration and deceleration capability of the scanning mechanism to achieve the targeted fast scan speed for a sufficient number of sparse regions, or regions of non-interest (RONIs), of the scanned area; and the capability of reliably detecting ROIs. More particularly, in microscopy applications using galvanometer-based scanning techniques, the selection of a ratio between the faster scan speed and the slower scan speed at which scan time is optimized, or at least improved, can be made depending on the anticipated number and extent of the RONIs, the achievable galvanometer acceleration and deceleration rates, and the signal-to-noise ratio of the signal at threshold value. For example, in some implementations, the ratio of the faster scan speed to the slower scan speed can range between two and ten.

Some general principles of the approach described above can be understood with reference to FIGS. 1A to 1F, which illustrate how an improved scanning efficiency may be achieved using ROI-predicted scan speeds.

Figure 1B:
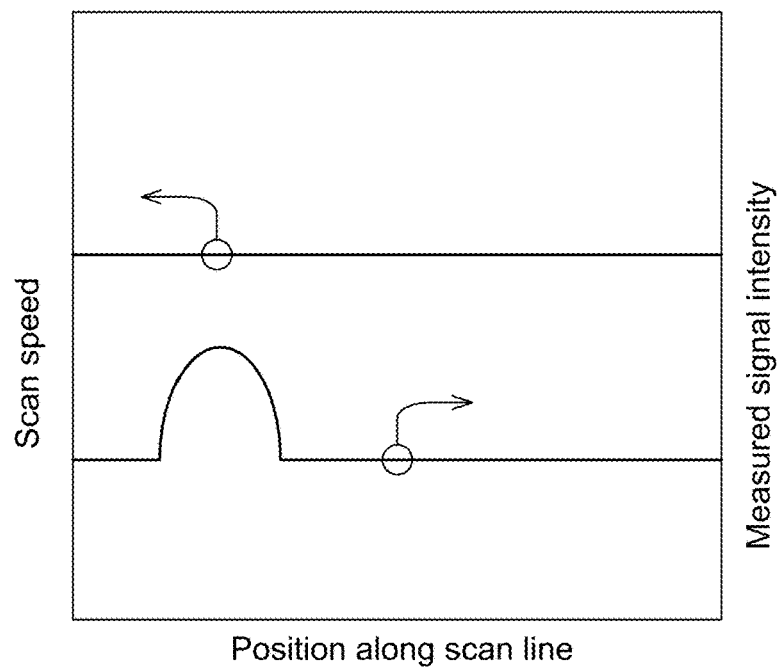
FIG. 1B (PRIOR ART) is a graph of the scan speed (left axis, arbitrary unit) and measured signal intensity (right axis, arbitrary unit) plotted as a function of position along the scan line for the topmost scan line in FIG. 1A (PRIOR ART).

FIG. 1A (PRIOR ART) is a schematic representation of a typical conventional raster scan measurement performed to obtain an image of a sample, in which all the scan lines 100' of the image are acquired at the same scan speed, regardless of the presence of ROIs 102' in the image. FIG. 1B (PRIOR ART) is a graph of the scan speed (left axis, arbitrary unit) and measured signal intensity (right axis, arbitrary unit) plotted as a function of position along the scan line for the topmost scan line 100a' in FIG. 1A (PRIOR ART). In contrast, FIG. 1C is a schematic representation of a raster scan measurement performed to obtain an image of a sample, in accordance with a possible embodiment, in which each scan line 100 of the image, except for the first one 100a, is acquired using a variable scan speed profile established based on the content of a previously acquired scan line. The variable scan speed profile includes a slower speed value (solid line) along segments of the scan line 100, corresponding to the predicted ROI positions, and a faster speed value (dashed line) elsewhere along the scan line 100.

Figure 1D:
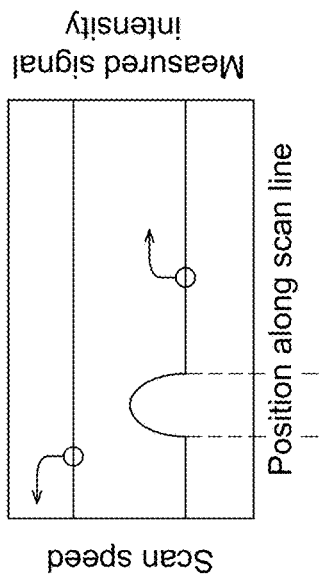
FIGS. 1D to 1F are a set of chronologically ordered graphs illustrating the scanning method used in FIG. 1C, in which the scan speed (left axis, arbitrary unit) and detected signal intensity (right axis, arbitrary unit) are plotted as a function of position along the first, second and third topmost scan lines in FIG. 1C, respectively.
Figure 1E:
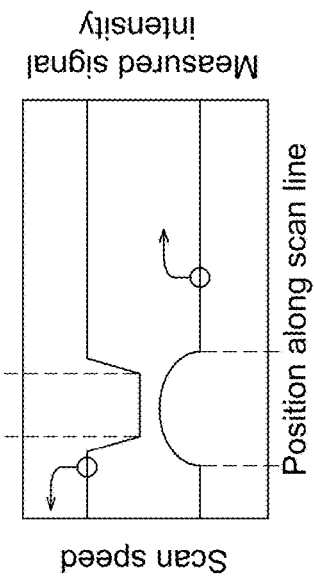
Figure 1F:
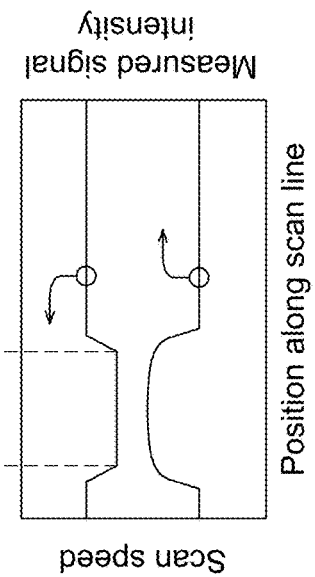
Figure 1C:
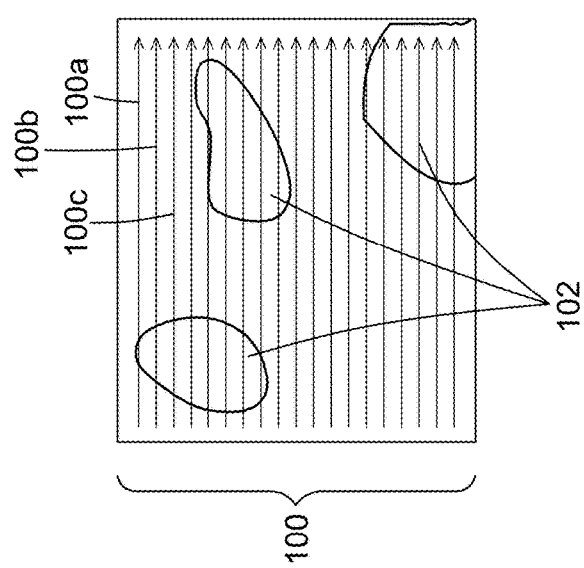
FIG. 1C is a schematic representation of a raster scan measurement to obtain an image of a sample, in accordance with a possible embodiment, where each scan line, except for the first one, is acquired using a variable scan speed profile determined based on the previously acquired predictive scan line.

FIGS. 1D to 1F present a set of chronologically ordered graphs illustrating the scanning strategy used in FIG. 1C, each graph plotting the scan speed (left axis, arbitrary unit) and detected signal intensity (right axis, arbitrary unit) as a function of position along a corresponding scan line in FIG. 1C (FIG. 1D: topmost scan line 100a in FIG. 1C; FIG. 1E: second topmost scan line 100b in FIG. 1C; and FIG. 1F: third topmost scan line 100c in FIG. 1C). Briefly described, the first scan line 100a is acquired at a constant scan speed, corresponding in this example to the slower speed value in subsequent scan lines. The measured intensity profile of the first scan line 100a is used to predict the locations of ROIs 102 along the second scan line 100b, and the predicted ROI locations are used to determine the variable scan speed profile with which to acquire the second scan line 100b. The second scan line 100b is acquired next, using the variable scan speed profile thus determined, and its measured intensity profile is used to predict ROI locations along the third scan line 100c. These predicted ROI locations are then used to determine the variable scan speed profile with which to acquire the third scan line 100c, and so on. The process is continued until the last scan line of the image has been acquired. From FIGS. 1D to 1F, it is seen that the width of a peak associated with an ROI in the measured intensity profile of the $n^{th}$ scan line determines the length of a corresponding scan line segment acquired at the slower scan speed value in the $(n+1)^{th}$ scan line.

Figure 2:
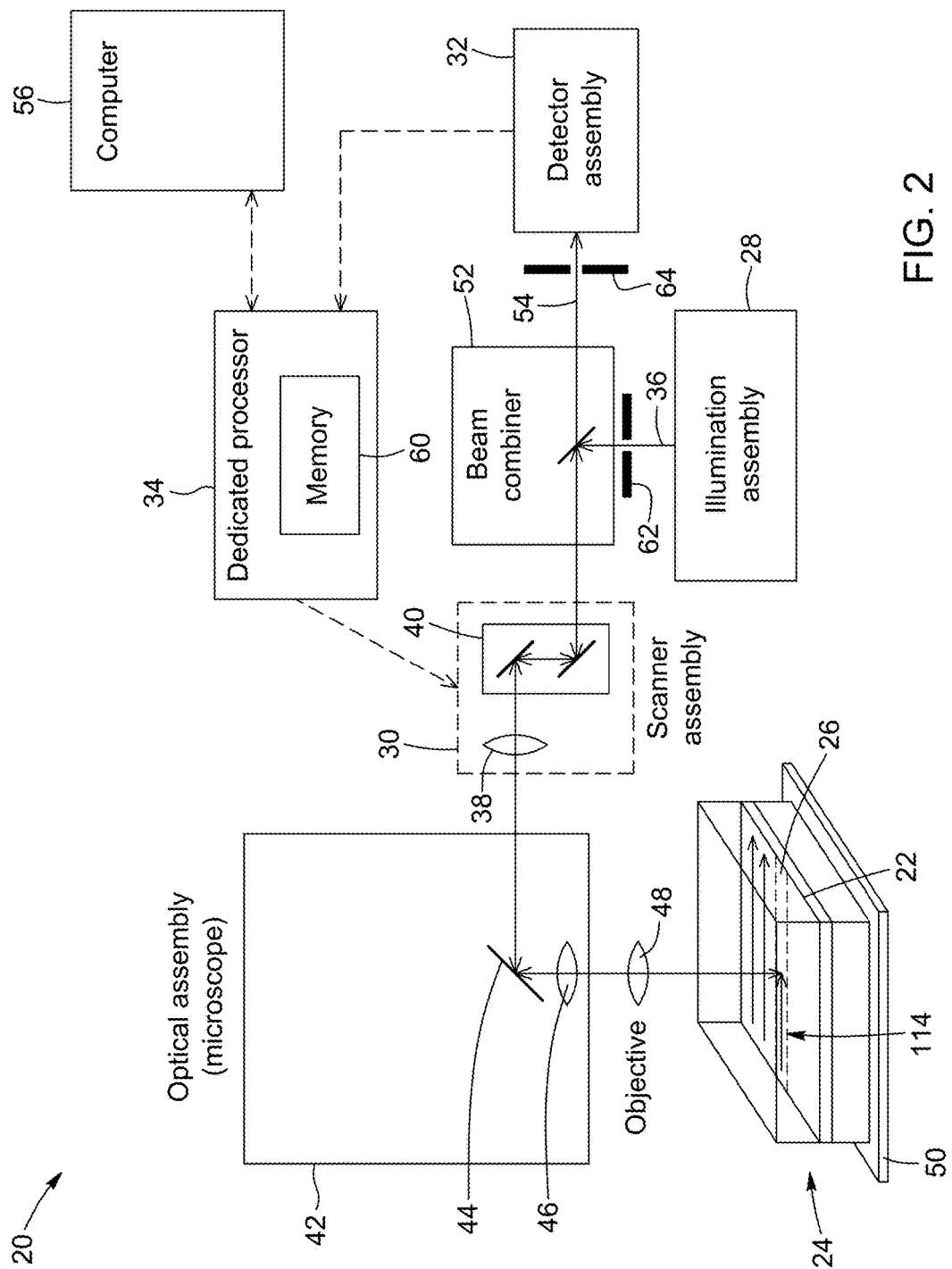
FIG. 2 is a schematic representation of an imaging system, in accordance with a possible embodiment. The imaging system in FIG. 2 is configured for confocal laser scanning microscopy.

Referring to FIG. 2, there is schematically illustrated an exemplary embodiment of imaging system 20 for obtaining an image of an object, namely an optical section 22 of a sample 24. The image includes a plurality of scan lines to be acquired, each of which corresponds to a respective section strip 26 of the optical section 22. In this embodiment, the image is acquired using confocal microscopy.

The illustrated imaging system 20 may be used to carry out the above-described approach using ROI-predicted scan speeds. Broadly described, the imaging system 20 of FIG. 2 can include an illumination assembly 28, a scanner assembly 30, a detector assembly 32, and a processor 34. The structure, configuration and operation of these and other possible components of the imaging system 20 will be described in greater detail below.

The illumination assembly 28 can be embodied by any appropriate device or combination of devices apt to generate an illumination or excitation beam 36 suitable for scanning-based optical imaging applications. For example, in some embodiments, the illumination assembly 20 can include a laser source generating a laser beam as the illumination beam 36. However, non-laser optical sources may be used in other embodiments including, but not limited to, light-emitting diodes (LEDs). The illumination beam 36 can be in the visible range or any appropriate region of the electromagnetic spectrum.

The scanner assembly 30 is configured to scan the illumination beam 36 along a scan path 114 over the optical section 22, to build the image thereof. In the illustrated embodiment, the scanner assembly 30 is configured to perform a multispeed raster scan of the illumination beam 36 to build the image of the optical section 22, pixel by pixel and scan line by scan line, as the illumination beam 36 is scanned successively over each section strip 26 of the optical section 22. As known in the art, each pixel represents the observation of a small and usually diffraction-limited region of the optical section to be imaged. The scanner assembly 30 can include a scan lens 38 and a pair of beam deflectors 40 disposed in the path of the illumination beam 36 to move the point of illumination of the illumination beam 36 in two dimensions over the optical section 22. In some embodiments, the beam deflectors 40 can be embodied by scanning mirrors such as, for example, servo-controlled galvanometric mirrors.

The detector assembly 32 is configured to detect light emanating from the optical section 22, and to generate from the detected light the image of the optical section 22, pixel by pixel. The detector assembly 32 can include one or more photodetectors, each of which is made up of an array of photosensitive elements capable of detecting electromagnetic radiation incident thereon, and of generating an image therefrom, typically by converting the detected radiation into electrical data. Depending on the application, various types of photodetectors can be used. For example, and without limitation, photomultiplier tubes (PMTs), silicon PMTs (SiPMTs), avalanche photodiodes (APD), charge-coupled-device (CCD) detectors, complementary metal-oxide-semiconductor (CMOS) detectors, and other high-quantum efficiency detectors can be used.

The processor 34 is configured to determine the positions of one or more predicted ROIs along each scan line of the image, based on at least one previously acquired predictive scan line. The processor 34 is also configured to control the scanner assembly 30 to scan the illumination beam 36 over the section strip corresponding to each scan line, in accordance with a variable scan speed profile. As mentioned above, the variable speed profile includes, for each scan line, at least one slower speed component along segments of the scan corresponding to the positions of the one or more predicted ROIs, and at least one faster speed component along other segments of the scan. Further details will be provided below regarding the prediction of ROIs in a currently acquired scan line from the identification of ROIs in a previously acquired scan line.

In the present description, the term "processor" denotes an entity of the imaging system that controls and executes, at least partly, functions required to operate the imaging system including, but not limited to, receiving data indicative of a previously acquired predictive scan line, determining from the received data predicted ROI positions of a scan line to be acquired, determining a scan speed profile or waveform for acquiring the scan line to be acquired; and supplying the scan speed waveform to a driver of the scanner assembly.

The processor 34 can be provided within one or more general purpose computers and/or within any other suitable computing devices. It should be noted that the term "processor" should not be construed as being limited to a single processor, and accordingly, any known processor architecture may be used. The processor 34 can be implemented in hardware, software, firmware, or any combination thereof, and be connected to various components of the imaging system via appropriate communication ports.

The processor 34 may implement operating systems, and may be able to execute computer programs, also generally known as commands, instructions, functions, processes, software codes, executables, applications, and the like. It is to be noted that in some implementations, a processor said to be configured to perform one or more commands, instructions, and the like may correspond to a configurable processor circuit fabricated, designed or "wired" to perform the commands, instructions, and the like. For example, such a processor circuit can be a field-programmable gate array (FPGA).

The processor 34 may include or be coupled to one or more memory elements 60 capable of storing computer programs and other data to be retrieved by the processor 34. The or each memory element 60 can also be referred to as a "computer-readable storage medium".

In some implementations, the processor 34 can be a fast, dedicated processor such as an FPGA with associated analog-to-digital input converter and digital-to-analog output converter. Using a dedicated processor such as an FPGA may be useful in high-speed scanning applications, where it may be required or desired to process recorded pixel count values and compare them to a threshold at sufficiently high rate, to not adversely affect or limit the overall image acquisition process. However, in other implementations, the processor 34 may alternatively or additionally include other types of processing elements, such as a microprocessor, a microcontroller, a coprocessor, a central processing unit (CPU), an image signal processor (ISP), a digital signal processor (DSP) running on a system on a chip (SoC), or any other type of processing element, or any combination of such processing elements configured to operate collectively as a processor.

Referring still to FIG. 2, the imaging system 20 may also include an optical assembly 42, such as an optical microscope. In this embodiment, the optical microscope is a confocal microscope, such that the imaging system 20 includes an illumination pinhole 62 in front of the illumination assembly 28 and a detection pinhole 64 in front of the detector assembly 32. The optical assembly 42 includes imaging optics to receive the illumination beam 36 from the scanner assembly 30 and to focus it onto the sample 24. In the illustrated embodiment, the optical assembly 42 is depicted as including a turning prism 44 for redirecting the illumination beam 36 received from the scanner assembly 30, a tube lens 46, and an objective 48. It should be noted that the general principles underlying the structure and operation of conventional confocal microscopes are known in the art, and need not be covered in detail herein.

The imaging system 20 of FIG. 2 may further include a sample holder 50 configured to support the sample 24 to be imaged; a beam combiner 52, for example a dichroic mirror, to provide confocal overlap between the illumination beams and detection or emission beam 54 between the scanner assembly 30 and the sample 24; and a computer 56 to perform and control various operations in the imaging system 20, for example, and without limitation, setting initial scan parameters, controlling sample stage motion, and receiving image data. Of course, other embodiments may include different or additional components, without departing from the scope of the present description.

Figure 3:
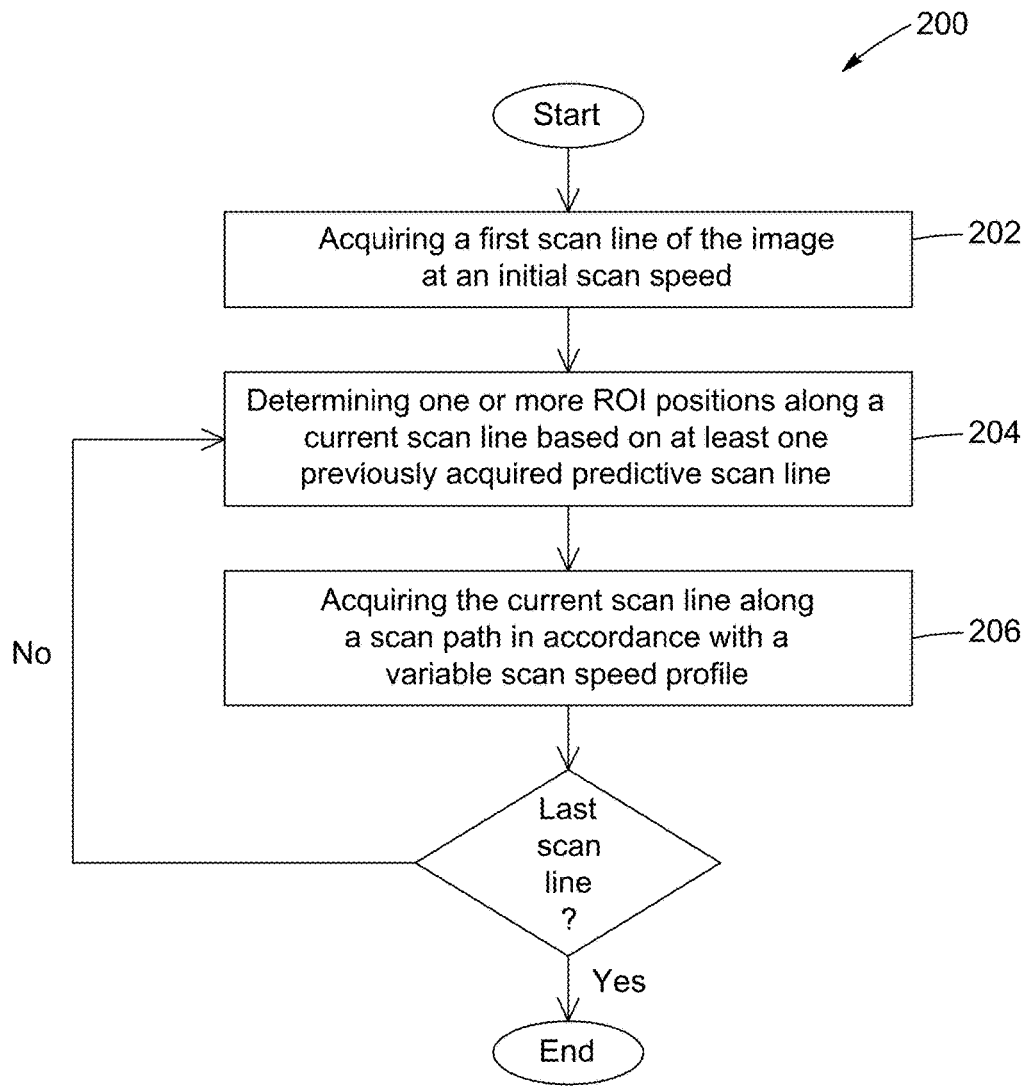
FIG. 3 is a flow diagram of a method for obtaining an image of an optical section of a sample, in accordance with a possible embodiment.

Referring now to FIG. 3, there is provided a flow diagram of a possible embodiment of a method 200 for obtaining an image of an object, for example an optical section of a sample, using raster-scan optical microscopy.

Figure 4:
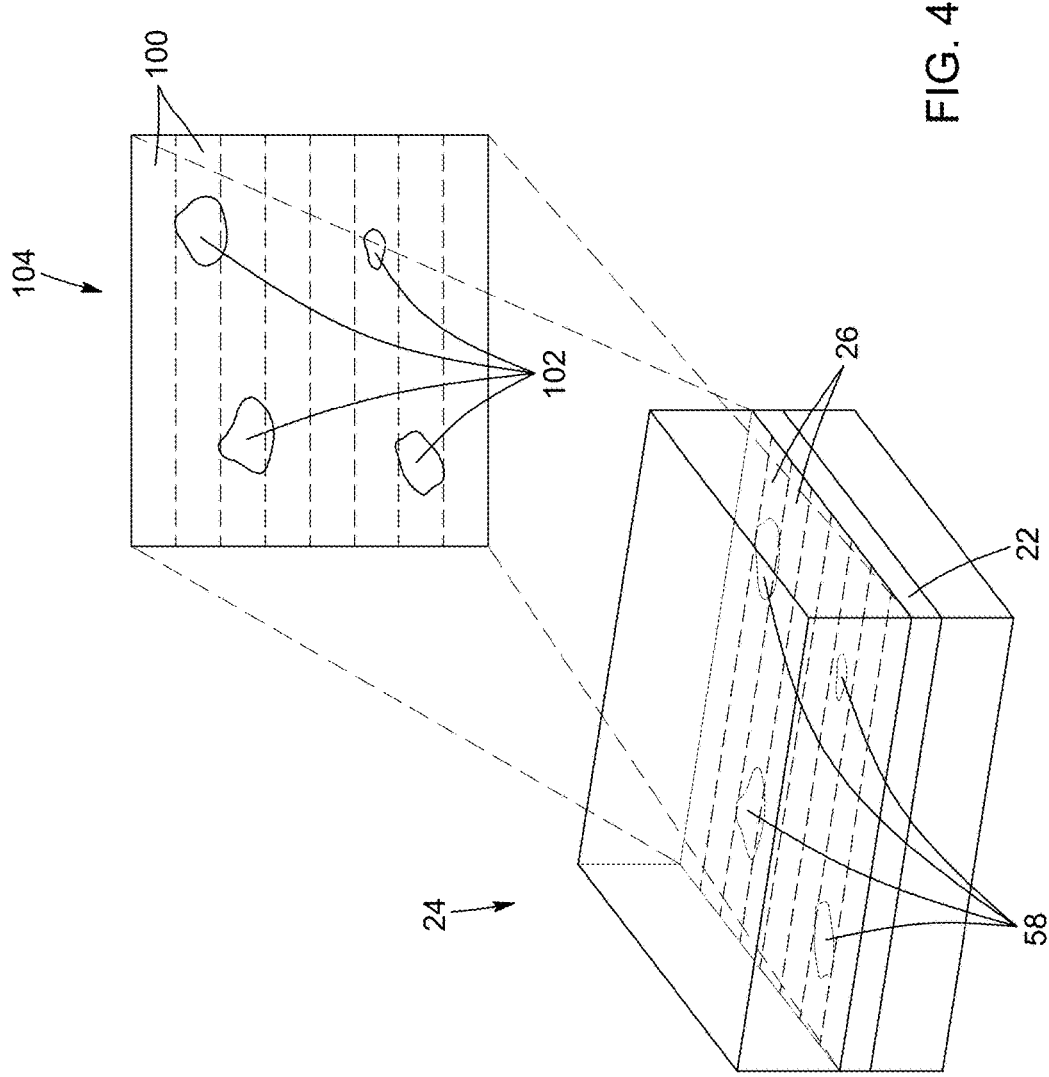
FIG. 4 is a schematic representation of a sample including an optical section to be imaged.

Turning briefly to FIG. 4, there is illustrated a schematic representation of an optical section 22 of a sample 24, as well as a corresponding image 104 of the optical section 22. It should be noted that the optical section 22 generally corresponds to a thin layer of material located at a certain depth inside the sample 24, so that the image 104 of the optical section is a 2D image. The image 104 includes a plurality of parallel scan lines 100, where each one of the scan lines 100 corresponds to a respective portion or section strip 26 of the optical section 22. The optical section 22 contains features of interest 58, for example cells, which are represented in the image 104. More particularly, each scan line 100 may include regions of interest 102, each region of interest 102 corresponding to at least part of a corresponding feature of interest 58 in the optical section 22. Building a 3D image of the sample 24 can be done by acquiring and combining a stack of 2D images at different depths across the sample 24.

Returning to FIG. 3, in some implementations, the method 200 can use single-point scanning confocal microscopy. Confocal microscopy generally involves point illumination of a sample with a laser beam, typically a diffraction-limited focal volume, the collection, detection and analysis of induced fluorescence generated from the interaction of the laser beam with the sample at the point of illumination, and the raster scanning of the laser beam over the sample to generate a 2D image of the sample. In confocal microscopy, one or more pinholes are placed in the path of the laser beam to block out-of-focus light, such that the image is acquired one depth level at a time. The laser beam is scanned over the surface of the sample, in a line-by-line sequence defining a raster scan pattern. The image is therefore made of a plurality of scan lines, each composed of a plurality of pixels. The raster scan pattern may be bidirectional, where successive lines are acquired along opposite directions, or unidirectional, where successive lines are acquired along a same direction with a "flyback" return of the scanning system to the starting side between each line. However, other detection modalities can be used in other embodiments and may include, for example, reflection-based imaging, transmission-based imaging, time-resolved and/or intensity measurements of fluorescence, phosphorescence, optical coherence tomography, photoacoustic, and other detection modalities arising from single-point scanning, and any combination thereof.

The method 200 can include a step 202 of acquiring a first scan line of the image at an initial scan speed. In general, this initial scan speed can be selected to be sufficiently slow to ensure that the first scan line has an acceptable signal-to-noise ratio. For example, in confocal microscopy, the initial scan speed can range between 10 and 10,000 optical degrees per second.

In the present method 200, the acquisition of the second and each subsequent scan line is carried out with a variable scan speed profile, which will generally differ from one scan line to the other. As described in greater detail below, the variable scan speed profile of each one of the second and subsequent scan lines can be determined by using predicted positions of ROIs along the scan line to be acquired, and by adjusting the scan speed such that the scan speed is slower along portions of the scan line where ROIs are predicted to be present and faster along portions of the scan line where ROIs are predicted to be absent. The present techniques provide an approach to predict ROI locations in the next scan line to be acquired which, for simplicity, will be referred to hereinbelow as the "current scan line".

Within this approach, the method 200 can include a step 204 of determining the positions of one or more predicted regions of interest along a current scan line based on at least one previously acquired scan line. In the present embodiment, the current scan line will be, successively, the second and each subsequent scan line of the image to be acquired. For example, the second scan line can be acquired at a variable scan speed that depends on predicted ROI locations inferred from data taken from the first scan line, and each subsequent scan line can be acquired at a variable scan speed that depends on predicted ROI locations inferred from data taken from one or more previously acquired scan lines.

For simplicity, it is noted that the previously acquired scan lines may sometimes be referred to herein as "predictive scan lines". As described in greater detail below, a given current scan line may be associated with one or more predictive scan lines, and each predictive scan line may or may not belong to the same image (e.g., optical detection channel) as the current scan line, and may or may not be acquired concurrently with the current scan line. In the present description, the term "concurrently" refers to two processes that occur during coincident or overlapping time periods. The term "concurrently" does not necessarily imply complete synchronicity, and encompasses various scenarios including: time-coincident or simultaneous occurrence of two processes; occurrence of a first process that both begins and ends during the duration of a second process; and occurrence of a first process that begins during the duration of a second process, but ends after the completion of the second process.

In some implementations, the step 204 of determining the positions of the one or more predicted ROIs can include steps of receiving each predictive scan line as a series of pixel intensity or count values ordered as a function of position along the predictive scan line; comparing, for each predictive scan line, the pixel values against one or more threshold criteria; and identifying the positions of the one or more predicted ROIs of the current scan line as, or based on, the positions of those pixel values that meet the one or more threshold criteria. Stated otherwise, the predicted ROI locations in the next scan line to be acquired can correspond to, or be based on, ROI locations determined in previously acquired scan line image data. In applications where the predictive scan lines belong to and are acquired during the same scanning session as the current scan line, the determining step 204 can include, prior to receiving each predictive scan line, a step of acquiring each predictive scan line.

In some implementations, the threshold criteria for identifying ROIs in a predictive scan line—and for predicting therefrom ROI locations in a corresponding current scan line—can be based on expected background noise levels. For example, in one embodiment, the detection limit for ROIs in a predictive scan line can be defined as greater than three standard deviations above the background noise level in the absence of analytes, targets or markers. Depending on the characteristics of the imaging system, the threshold criteria could be adjusted as a function of position within the field of view to account for vignetting, and other optical aberrations and distortions.

In some implementations, the threshold criteria can include a presence-absence threshold criterion according to which every pixel in a predictive scan line whose intensity is greater than a presence intensity threshold is predicted to belong in an ROI in the corresponding current scan line. For such a presence-absence threshold criterion, portions of the current scan line that lie between predicted ROIs will be scanned at a relatively faster rate. In other implementations, the threshold criteria may also, or alternatively, include a saturation threshold criterion according to which every pixel in a predictive scan line whose intensity is greater than a saturation intensity threshold is predicted to belong to a saturating ROI in the corresponding current scan line. Such a saturation threshold criterion can be used to predict the positions of regions within which pixel saturation is expected to occur along the current scan line. Therefore, by increasing scan speed over such predicted saturation regions, it may be possible to remain within the linear response range of the detector and avoid detector saturation. It should be noted that in some implementations, both a presence-absence threshold criterion and a saturation threshold criterion can be used at the same time, in which case the presence intensity threshold would be lower than saturation threshold. In yet other implementations, it is possible to use a threshold criterion based on a known varying background, or on fluorescence lifetime instead of intensity, or on a polarization ratio of detected light, and the like.

Referring still to FIG. 3, once the positions of predicted ROIs have been determined for the current scan line, the method 200 can include a step 206 of acquiring the current scan line by scanning its associated portion or section strip. The scan is performed along a scan path and in accordance with a variable scan speed profile of the current scan line. The variable scan speed profile can be established based on the identified positions of the one or more predicted ROIs. The variable scan speed profile includes at least one slower speed component along segments of the scan path corresponding to the positions of the one or more predicted ROIs and at least one faster speed component along other segments of the scan path (i.e., the RONIs). For example, in some embodiments, the step 206 of acquiring the current scan line can include scanning an illumination beam over the portion of the object or section strip corresponding to the current scan line in accordance with the variable scan speed profile; detecting an object signal (optical, acoustic or otherwise) emanating from the section strip; and generating the current scan line from the detected object signal. It should be noted that when no ROI is predicted to exist in a certain scan line, then this scan line may be acquired entirely at a faster scan speed.

In some implementations, the variable scan speed may exhibit a two-level switching behavior characterized in that, except for transition zones, it can only take on two nominal values, namely a slower nominal speed defining a single slower speed component and a faster nominal speed defining a single faster speed component. Depending on the application, the ratio of the faster nominal speed to the slower nominal speed can have various values, for example between two and ten. However, in other implementations, the variable scan speed can take on more than two values. For example, it may be envisioned that the variable scan speed profile be characterized by three possible scan speed components, namely a faster scan speed component used to scan RONIs, a first slower scan speed component used to scan a first type of ROI, and a second slower scan speed component different from the first slower scan seed component and used to scan a second type of ROI. In such case, the first and second types of ROIs could be distinguished in the predictive scan lines by employing appropriate image analysis techniques and/or imaging modalities.

Once the current scan line has been acquired, it becomes available for use as a predictive scan line, and the next scan line to be acquired becomes the new current scan line. In general, the determination and acquisition steps 204, 206 can be repeated for each successive scan line until the acquisition of the image of the optical section has been completed. In some implementations, the determination and acquisition steps 204, 206 for successive scan lines can be executed in parallel and in real-time. That is, the acquisition step 206 for one scan line can be carried out concurrently with the determination step 204 for the next scan line, thus enabling continuous acquisition with inline processing.

More details regarding various other possible features of the present techniques will now be described.

In some implementations, each predictive scan line involved in the prediction of ROI locations along a current scan line can be a previously acquired scan line that belongs to the same image as the current scan line. In such implementations, various scenarios are possible.

Figure 5:
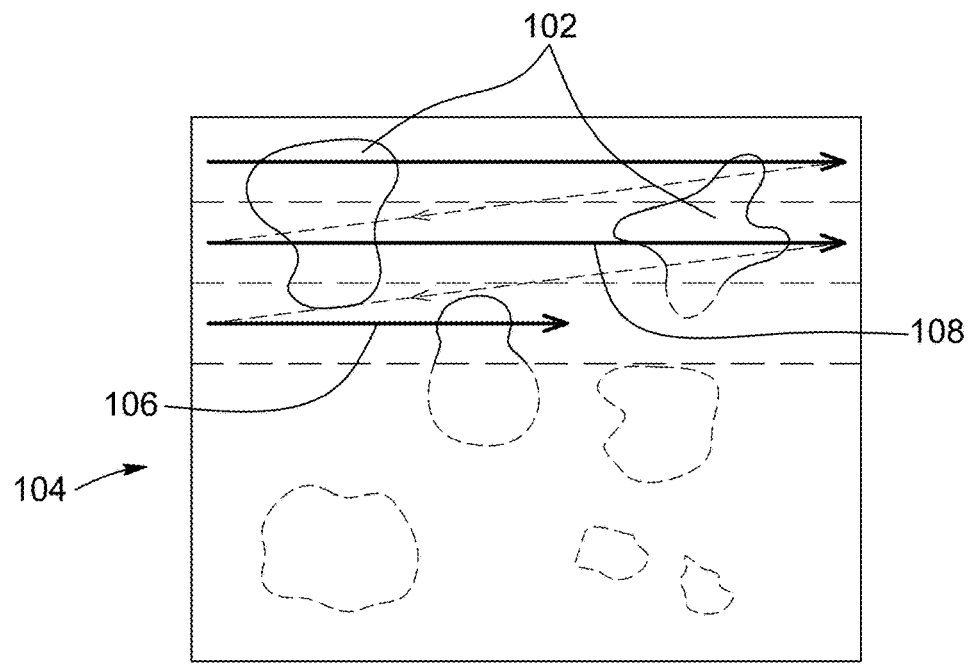
FIG. 5 is a schematic representation of the acquisition of a current scan line of an image of an optical section, in accordance with a possible embodiment, wherein the at least one predictive scan line associated with the currently acquired scan line is the scan line acquired immediately before the currently acquired scan line.

Referring to FIG. 5, in the simplest case, a current scan line 106 of the image 104 can be associated with a single predictive scan line 108, which corresponds to the scan line closest to and acquired immediately before the current scan line 106.

Figure 6:
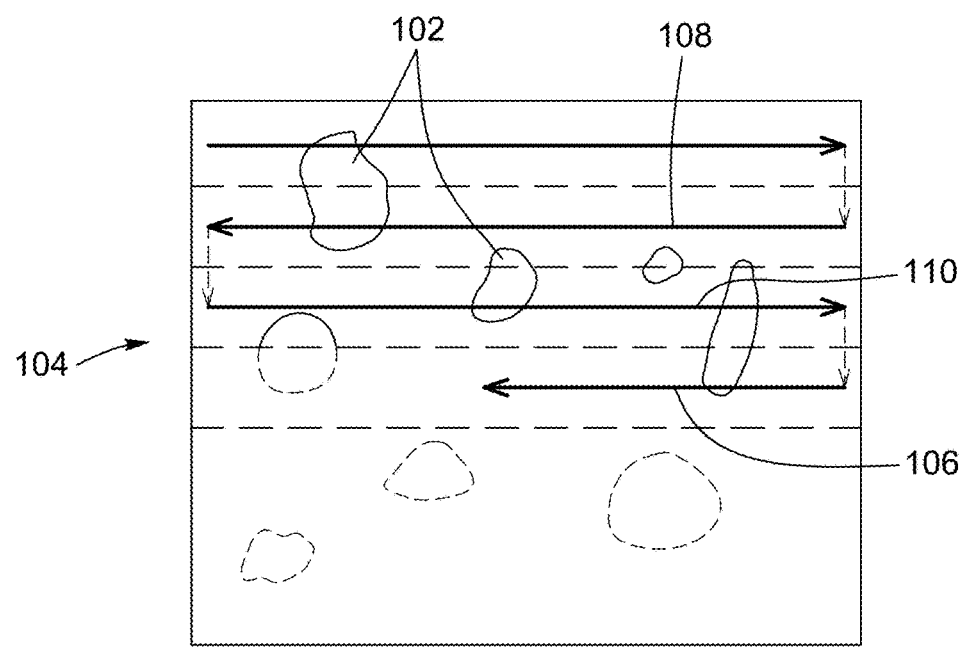
FIG. 6 is a schematic representation of the acquisition of a current scan line of an image of an optical section, in accordance with a possible embodiment. This embodiment uses a bidirectional raster scan in which adjacent scan lines of the image are scanned along opposite directions. In this embodiment, the currently acquired scan line and its associated predictive scan are scanned along the same scanning direction and are separated from each other by one intervening scan line scanned in the opposite scanning direction.

However, the present techniques are not limited to using data from the immediately preceding scan line to predict ROI locations of the next scan line. Indeed, in some applications, a current scan line and its associated predictive scan line can have one or more intervening scan lines therebetween. For example, referring to FIG. 6, some embodiments can use a bidirectional raster scan in which adjacent scan lines of the image 104 are scanned along opposite directions. In such a case, the predictive scan line 108 associated with the current scan line 106 may be the last scan line scanned in the same scanning direction as the current scan line 106. The current and predictive scan lines are therefore separated from each other by one intervening scan line 110 scanned in the opposite scanning direction.

Figure 7:
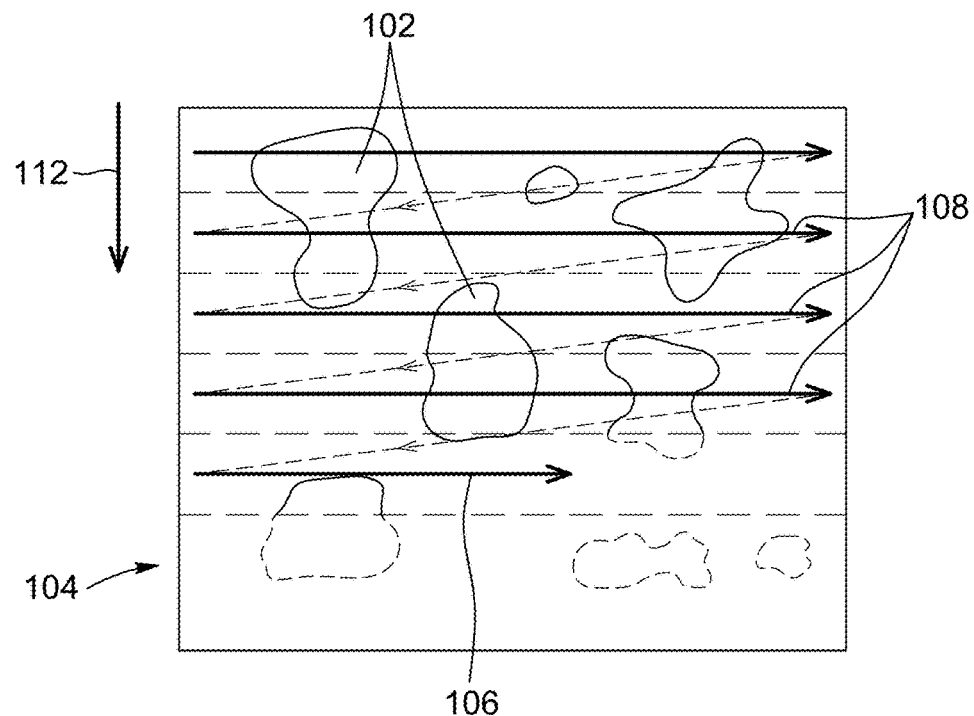
FIG. 7 is a schematic representation of the acquisition of a current scan line of an image of an optical section, in accordance with a possible embodiment, wherein the at least one predictive scan line associated with the currently acquired scan line consists of the three scan lines of the image acquired immediately before the currently acquired scan line.

In some implementations, ROI locations in the current scan line 106 could be predicted based on two or more predictive scan lines 108, each of which corresponds to a previously acquired scan line belonging to the same image (e.g., detection channel) as the current scan line. For example, referring to FIG. 7, some embodiments can predict ROI locations along the current scan line 106 based on a local gradient along the slow axis 112. This process could involve analyzing, for each pixel position in the current scan line 106, pixel data from the same pixel position in a plurality of previously acquired scan lines 108. In the embodiment of FIG. 7, the predictive scan lines are the three scan lines 108 of the image 104 acquired immediately before the currently acquired scan line 106.

Figure 8:
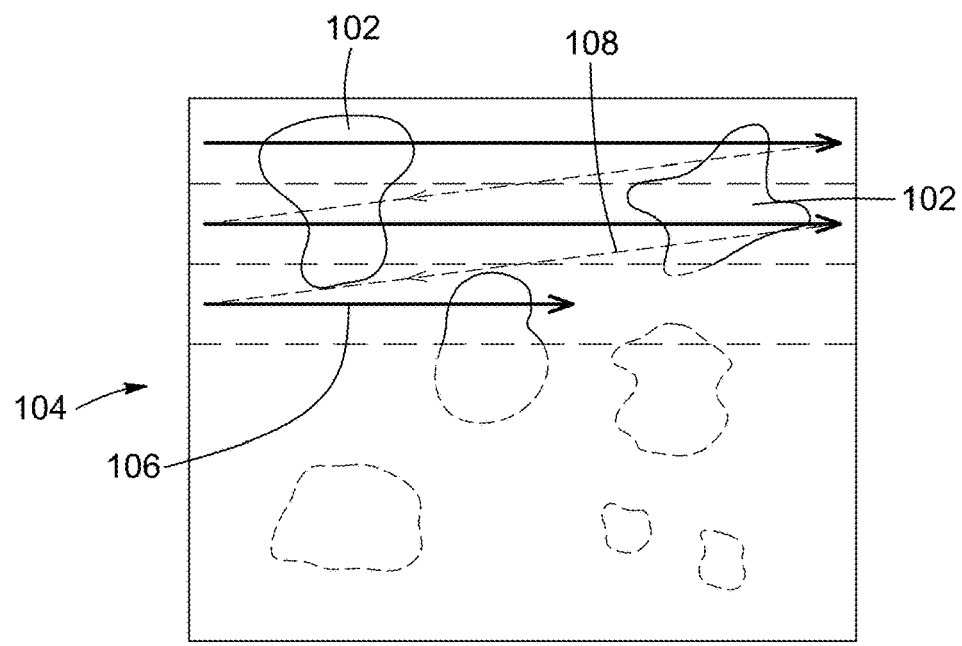
FIG. 8 is a schematic representation of the acquisition of a current scan line of an image of an optical section, in accordance with a possible embodiment. This embodiment uses a unidirectional raster scan including a flyback return between each pair of successive scan lines. In this embodiment, a flyback scan line is acquired during each flyback return, and the at least one predictive scan line associated with the currently acquired scan line is the flyback scan line acquired immediately before the currently acquired scan line.

In further implementations, the at least one predictive scan line may not be a previously acquired scan line belonging to the same image as the current scan line. For example, referring to FIG. 8, some embodiments can use a unidirectional raster scan including a flyback return between each pair of successive scan lines. In such embodiments, the predictive scan line 108 associated with the currently acquired scan line 106 can be acquired during the flyback return between the currently acquired scan line 106 and the scan line acquired immediately before it. In such a case, the predictive scan line 108 can be referred to as a "flyback scan line". In some applications, it may also be envisioned to use a set of multiple flyback scanlines as predictive scan lines.

The present techniques can also be used in multimodality imaging. In such applications, multiple image acquisitions can be made with the same imaging system, each image acquisition corresponding to a different imaging modality and having its own detection channel. The multiple image acquisitions may be carried out simultaneously, concurrently, sequentially, or by interleaving of detection channels. In some implementations, one detection channel or a combination (e.g., arithmetic) of several detection channels may be used for determining predicted ROIs and establishing therefrom a scan speed profile that can be applied to all the detection channels. This or these detection channels can be referred to as "master detection channels". The images associated with other detection channels can be acquired using the scan speed profile determined by the one or more master detection channels, without having to recalculate another scan speed profile. These other images can be acquired simultaneously or concurrently with the images associated with the master detection channels, or through subsequent "replays" of the master scan speed profile. Depending on the application, the master scan speed profile can be replayed for the other detection channels on a line-by-line, an image-by-image or a stack-by-stack basis.

Other non-limiting possible examples of multimodality implementations will now be described, which differ in the type of the at least one predictive scan line used to predict ROI locations in a current scan line of an image to be acquired with one of the detection channels.

Referring to FIGS. 9A and 9B, in some implementations, the image 104 containing the current scan line 106 (FIG. 9A) and the image(s) 116 containing the at least one previously acquired predictive scan line 108 (FIG. 9B) can be acquired using two or more distinct detection channels and a single illumination source. For example, two detection channels can be used to measure fluorescence emission simultaneously using the same excitation beam. One detection channel can be a master detection channel (image 116 in FIG. 9B) from which a scan speed profile can be established by determining predicted ROI locations from one or more previously acquired scan lines 108. Because a single excitation beam is used, the scan speed profile established from the master detection channel is used for both detection channels (both the image 104 in FIG. 9A and the image 116 in FIG. 9B). It should be noted that the expression "distinct detection channels" can refer to both the case of two or more physically distinct detection channels provided on two or more separate detectors, and the case of two or more distinct data streams acquired on a single physical detector, for example where different acquisitions are performed at different frequencies and/or at different acquisition times using time-alternating illumination pulses. In the second case, such distinct detection channels may be referred to as "virtual detection channels" to denote the fact that two or more channels of information can be acquired using a single physical channel.

Figure 10A:
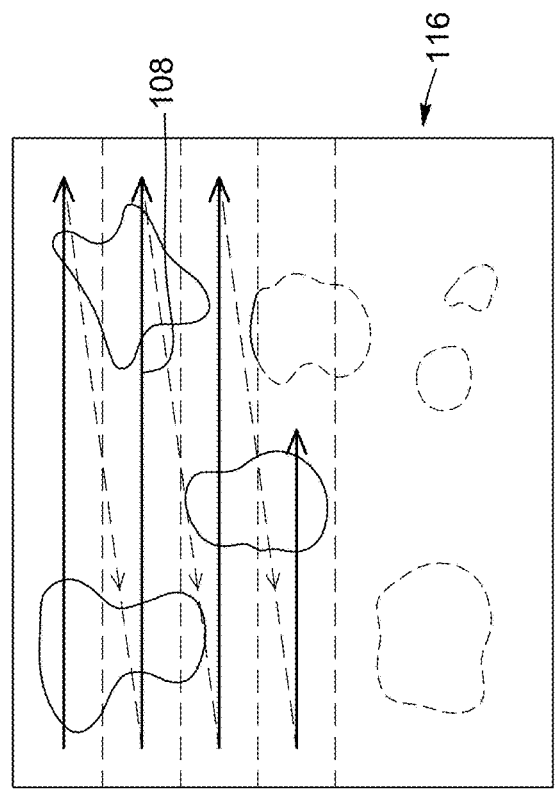
FIGS. 10A and 10B are schematic representations of the acquisition of a current scan line of an image (FIG. 10A) of an optical section, in accordance with a possible embodiment, wherein the at least one predictive scan line associated with the current scan line belongs to another image (FIG. 10B), acquired using a different detection channel and a different illumination source than the image containing the current scan line.
Figure 10B:
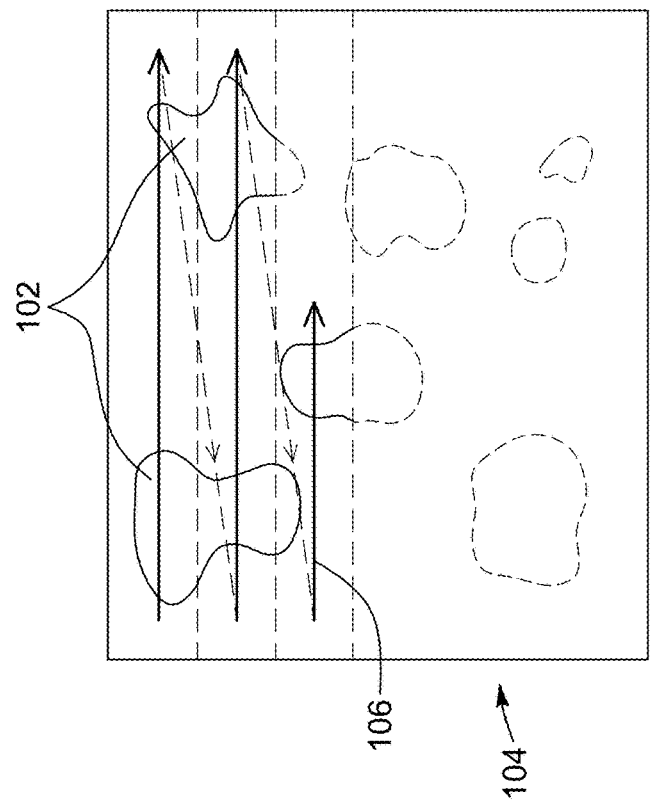

Referring to FIGS. 10A and 10B, in other implementations, the image 104 containing the current scan line 106 (FIG. 10A) and the image(s) 116 containing the at least one previously acquired predictive scan line 108 (FIG. 10B) can be acquired using two or more distinct detection channels and two or more distinct illumination sources. For example, in some embodiments, two corresponding illumination beams can be scanned over the object to be imaged, along either spatially coincident or spatially offset scanning paths. For example, in the latter scenario, the spatially offset scanning paths can be offset along the slow axis by one or a few scan lines. In this case, a scan line acquired by the detection channel associated with the leading illumination beam (FIG. 10B) can be used as a predictive scan line 108 to establish the variable scan speed profile with which to scan the leading illumination beam over the next scan line to be acquired. This scan speed profile can be used shortly thereafter to acquire the same scan line 106 with the lagging illumination beam (FIG. 10A).

In yet other implementations, the at least one previously acquired predictive scan line can include multiple spatially registered predictive scan lines acquired using multiple detection channels, one of which may, but need not, belong to the image containing the current scan line. As used herein, the term "spatially registered" means that the multiple predictive scan lines associated with a current scan line correspond to line images of a same area (e.g., section strip or portion) of the optical section or object to be imaged. For example, referring to FIGS. 11A and 11B, the image 104 containing the current scan line 106 includes a first predictive scan line 108a (FIG. 11A) and another image 116, acquired with another detection channel, includes a second predictive scan line 108b (FIG. 11B). The first and second predictive scan lines 108a and 108b are spatially registered and acquired at the same time using the same or a different illumination source. In such implementations, the determination of predicted ROI positions along the current scan line associated with the multiple detection channels can include a step of verifying, for each potential ROI, whether a specified condition (e.g. a threshold condition) is met for at least one of the multiple spatially registered predictive scan lines before identifying this potential ROI as a predicted ROI. This means that, depending on the application, a single, at least some, or all of the predictive scan lines may be required to meet the specified condition for a potential region of interest to be considered as a predicted region of interest. Combinations of predictive scan lines from multiple detection channel responses may be used in a threshold algorithm to determine ROIs. For example, in an application where identifying colocalization of fluorophores A and B is of interest, a threshold algorithm could be applied according to which an ROI is predicted to exist only if the measured signal exceeds a threshold level in both a first detection channel associated with fluorophore A and a second detection channel associated with fluorophore B.

With respect to the variable scan speed profile, in some implementations a condition may be set that a minimum scan path distance should exist between two ROIs for the space therebetween to be considered a RONI, and therefore scanned at a fast scan speed. Using such a condition can ensure or help ensure that only scan line segments longer than a predetermined or specified threshold will lead to a scan speed transition from a slower to a faster speed, and can therefore avoid making scan speed transitions to higher scan speeds that would provide only negligible time savings, if any. In general, the scan speed transition profiles of a given scanner can be known in advance to ensure or help ensure that sufficient settle time is given prior to the scanning of a predicted ROI. Smoothing of output data using known filtering strategies such as, for example, median filters, may be used to reduce threshold transitions due to noisy images.

In some implementations, the determination of the variable scan speed profile of the current scan line is made based on predicted ROI locations identified in previous scan lines which are themselves also acquired at variable scan speeds. The analysis of image data from those previous scan lines for ROI identification purposes can account for these variable acquisition speeds, for example by considering that longer dwell times over a pixel will lead to greater pixel counts for that pixel. Therefore, a normalization of the detected predictive scan line image data may be performed to ensure that ROIs can be detected at 'slower', 'faster' and transitional speeds. In some implementations, the scan speed profile for a given predictive scan line may be determined via knowledge of the scan profile sent to the galvanometers for this line, considering the frequency response of the galvanometer mirrors, or from data measured by a position or velocity sensor included in the galvanometers of the scanner assembly.

In some implementations, various scan parameters can be predetermined, that is, determined prior to a scanning session, including slower and faster scan speed values, acceleration and deceleration rates of the scanner assembly, and ROI threshold criteria.

The overall improvement in scanning time that may be achievable by the present techniques can depend on various factors, for example the sparsity of the image; the speed difference between the slower and faster scan speeds; and the achievable acceleration and deceleration rates to go from the slower to the faster scan speed, and vice versa. Some implementations may cause some information to be lost at the very edges of ROIs where the signal is above the threshold, but was not predicted to be, based on the analysis of a previous acquired scan line. However, the increased noise resulting from these pixels being scanned at a higher speed than they should have been can remain acceptable in many high-resolution applications. Indeed, this increased noise often cannot be perceived by the naked eye in the resulting image, as ROI edge pixels generally have count values significantly lower than ROI center pixels.

In some implementations, the acceleration and deceleration of galvanometer mirrors in accordance with the variable scan speed profile of the current scan line can cause an offset between the instantaneous output command position and the actual mirror position. This can create an offset between the portions of the image acquired at a faster scan speed and those acquired at a slower scan speed when the image is built based on mirror output command curves. If left uncorrected, this speed-based spatial offset may produce undesirable or unacceptable artifacts in the image. In some embodiments, this offset can be corrected by modifying acceleration and deceleration pixel dwell times. In other embodiments, a correction may also, or alternatively, be performed in post-processing of the image, by aligning the pixels acquired at faster scan speeds with those acquired at slower scan speeds, which can be done by shifting the "faster" pixels with respect to the "slower" pixels, with "transition" pixels being stretched or compressed to accommodate the under or oversampled data occurring the acceleration and deceleration portions of the scan line.

In some implementations, the digitized input from the detector—whether digitized by an external ADC, a photon counter, a time-correlated photon counter, or other means—can be binned to ensure that both the number of digital acquisitions made at the slower scan speed and the number of digital acquisitions made at the faster scan speed result in a whole number for each pixel. Furthermore, transition ramps between slower and faster scan speeds may be selected to ensure that a whole number of digitized data points are acquired during each transition ramp. Scan speed transitions may also be adjusted to ensure that the position offset of the galvanometric mirrors between the faster and slower scan speeds results in a whole number of pixels in each transition ramp.

Figure 12:
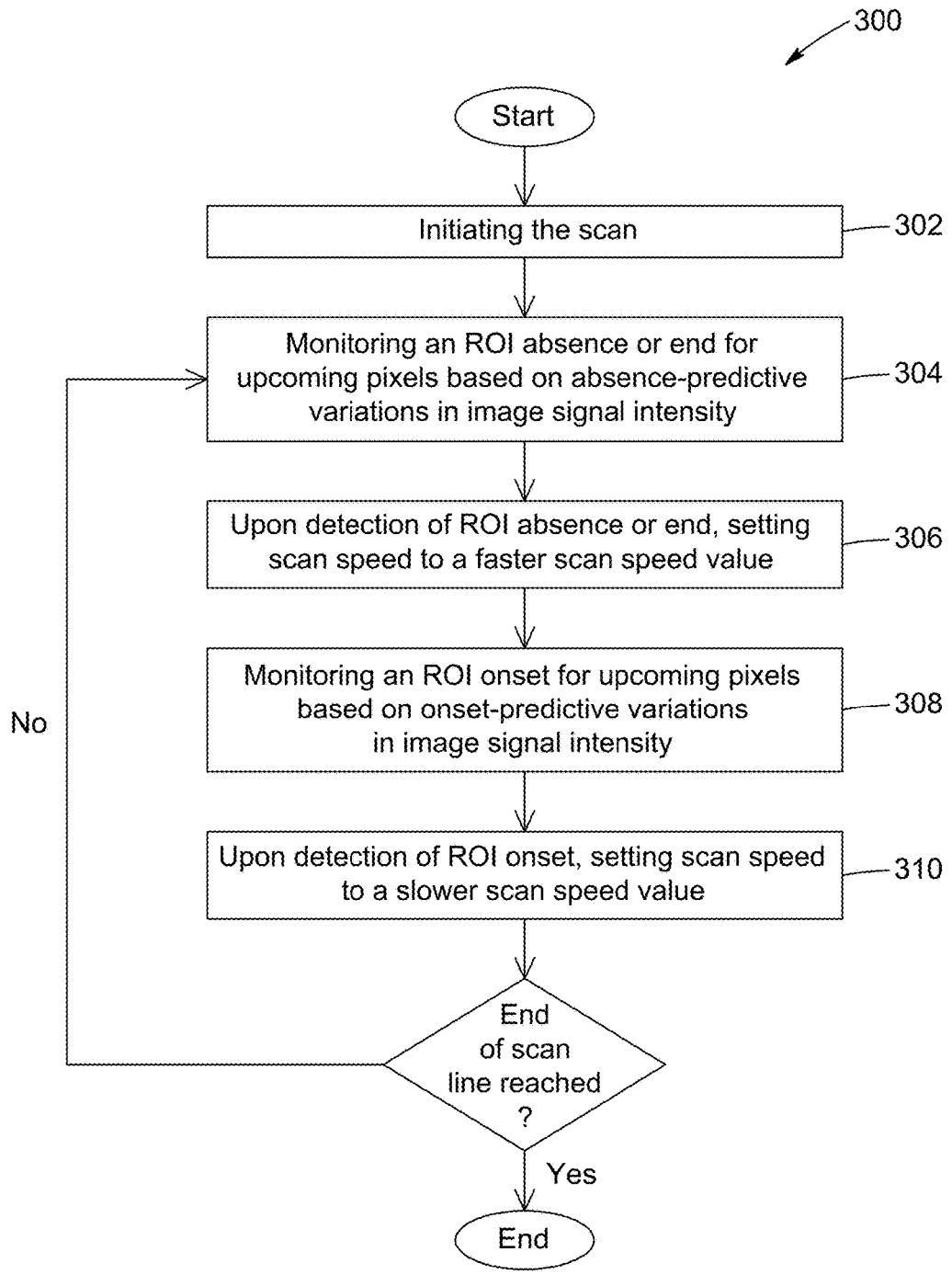
FIG. 12 is a flow diagram of a method of performing a scan for acquiring a scan line of an image of an optical section of a sample, in accordance with a possible embodiment.

In accordance with another aspect, there is provided a method of performing a scan for acquiring a scan line of an image of an object, for example an optical section of a sample. The scan line corresponds to a respective portion or section strip of the object. In this method, previously acquired image data from a current scan line may be used to predict the ROI boundaries before they occur. With sufficiently high processing speeds, the beginning and the end of an ROI may be detected, for example from a change in a gradient of the detected signal. A possible embodiment of the method 300 is illustrated in the flow diagram of FIG. 12. The method 300 can include a step 302 of initiating the scan at a scan speed, generally a slower scan speed. The method 300 can also include a step 304 of monitoring an absence or an end of an ROI for upcoming pixels of the scan line based on absence- or end-predictive variations in image signal intensity. Upon detection of such an absence or end, the method 300 can include a step 306 of setting the scan speed to a faster scan speed value. The method 300 can next include a step 308 of a monitoring an onset of an ROI for upcoming pixels of the scan line based on onset-predictive variations in image signal intensity. Upon detection of such an onset, the method can include a step 310 of setting a scanning speed to a slower scan speed value. The method 300 can then include repeating the monitoring steps 304, 308 until the end of the scan line is reached.

Figure 13A:
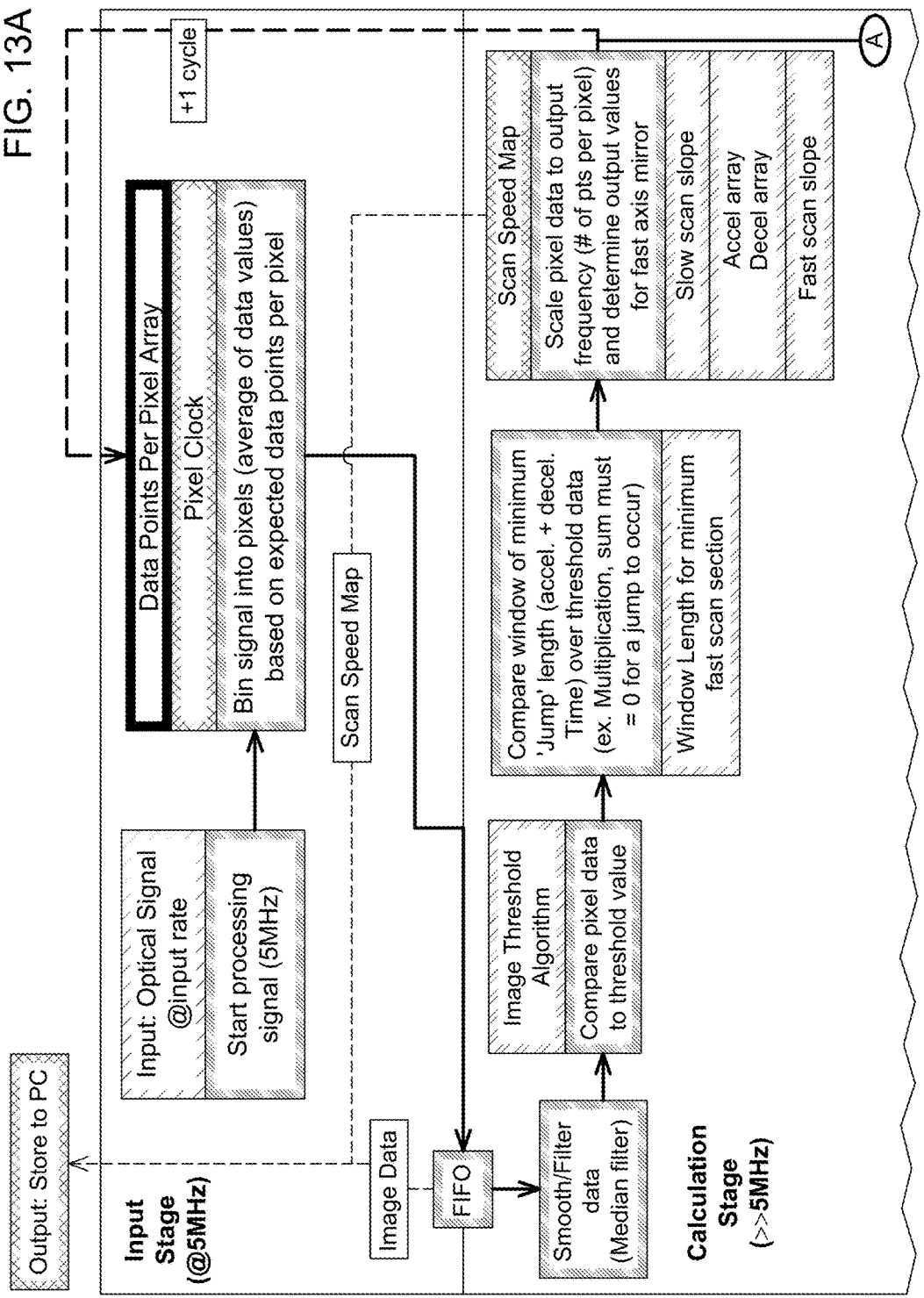
FIGS. 13A and 13B are the top and bottom parts of a flow diagram of an algorithm stored or programmed in a field-programmable gate array (FPGA), in accordance with a possible embodiment. The FPGA is configured to control and execute, at least partly, functions for acquiring images with a scanning imaging system.
Figure 13B:
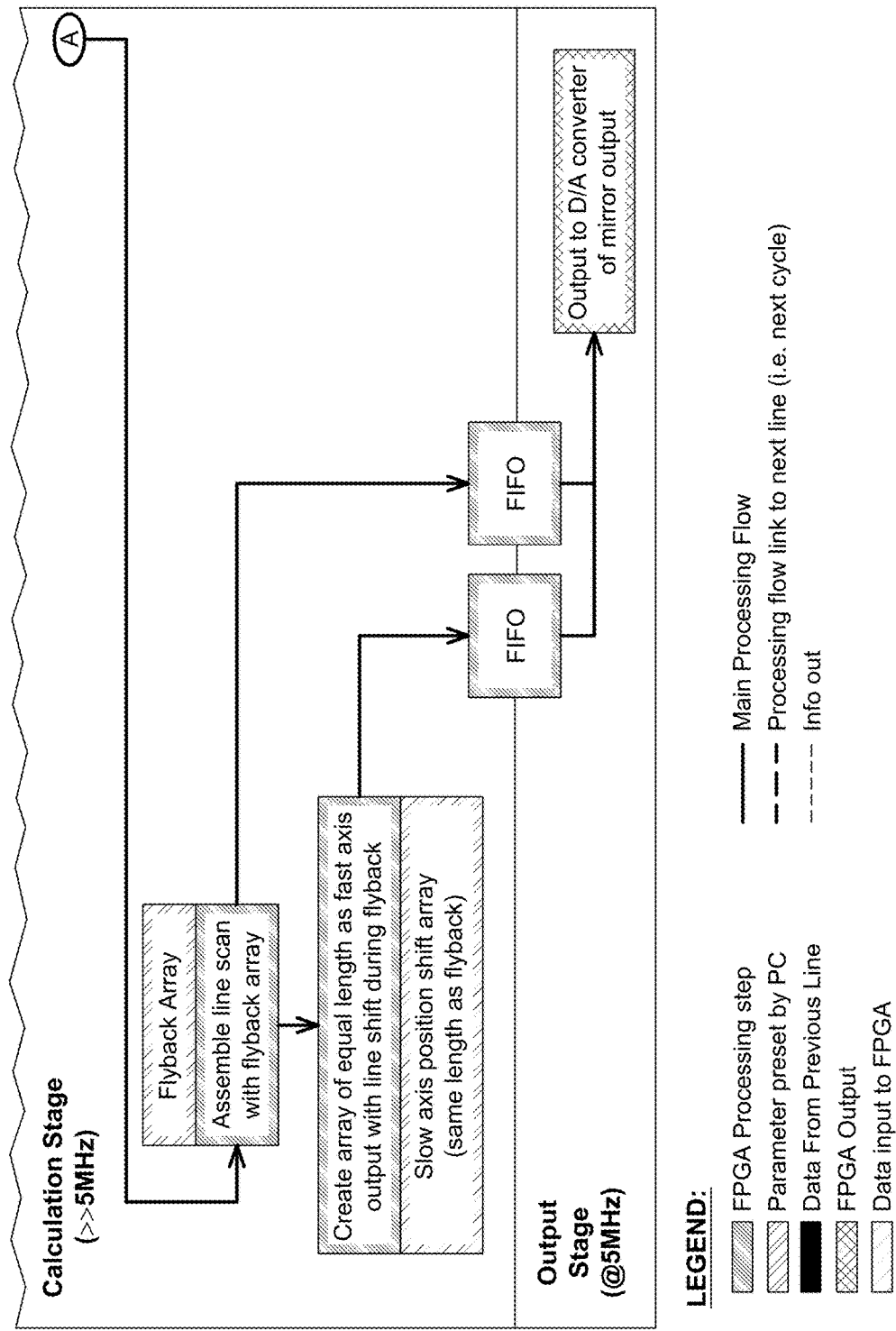

Returning to FIG. 2, in one implementation of the present techniques using unidirectional raster scanning with ROI predictions based on previously acquired raster scan lines, a high-resolution microscope 42 with automated stage translation may be used to image a plurality of locations within a multiwell plate. A high numerical aperture (>0.2 NA) objective 48 and a tube lens 46 may be used to define a field of view for the scanned illumination beam 36. A scanner assembly 30 comprising two independent non-resonant galvanometer actuated mirrors 40 and a scan lens 38, scans the illumination beam 36 in a raster format into the microscope 42. The scanner axes are driven by galvanometer servo drivers, which receive instruction from the dedicated processor 34 in the form of an FPGA with associated analog-to-digital converter (ADC) and digital-to-analog converter (DAC). An example of an algorithm executed by an FPGA processor is shown in FIGS. 13A and 13B. A first scan line acquired at a constant "slower" speed is provided to obtain an initial determination of the location of ROIs, after which a detector output for each successive scan line of the raster scan is used to predict the ROI locations of a following scan line, and thus the scan speed profile. The output of the detector assembly 32 is converted into a digital count per clock period of the dedicated processor 34, and this information is processed, allowing the calculation of future scan speed profiles to be sent to the fast-axis galvanometer servo driver. An illumination assembly 28 produces an illumination beam 36 along an illumination path overlapped in a confocal configuration with the detection path using a beam combiner 52, for example a dichroic filter. Image reconstruction may be performed based on a pixel clock determined based on the galvanometer position feedback signal or the galvanometer command signal, to provide pixel timing, and on scan speed, to normalize the signal intensity.

Figure 14A:
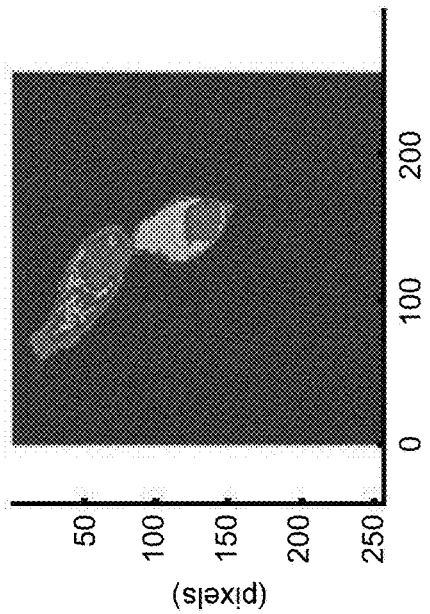
FIG. 14A is an image of cells acquired by single-beam scanning confocal microscopy.
Figure 14B:
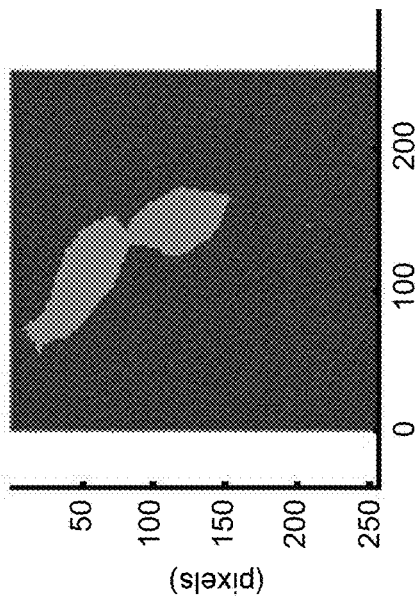
FIG. 14B is an intensity image obtained through in silico modeling, in accordance with a possible embodiment.
Figure 14C:
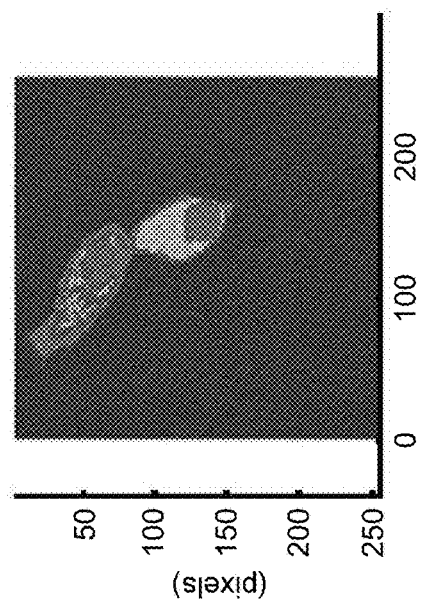
FIG. 14C is a variable scan speed map obtained from applying a threshold-based analysis to FIG. 14A.
Figure 14D:
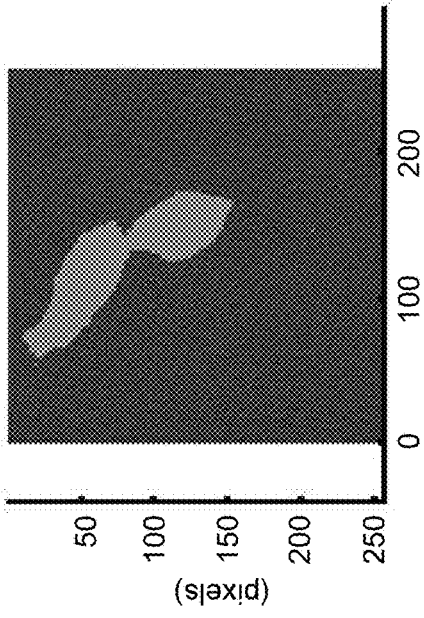
FIG. 14D is a corrected threshold image obtained from FIG. 14C and accounting for real-world properties and limitations of galvanometer mirrors.

In such a system, a mathematical model based on the experimental performances of a X-Y galvanometer scanner has shown that by using a reasonable increase (e.g., a fourfold increase) in scan speed over ROIs compared to RONIs, the present techniques can yield a significant (e.g., greater than 40%) reduction in scan time in the analysis of real cellular images obtained from a confocal fluorescence imaging microscopy image set (512×512 pixels, 0.25 frame per second). FIGS. 14A to 14D provide an example of such scan-time reduction capabilities. FIG. 14A is a cellular image acquired by single-beam scanning confocal microscopy. FIG. 14B is an intensity image obtained through in silico modeling, using an embodiment of the present techniques based on predicted ROI locations. The modeled cellular image of FIG. 14A was compared pixel by pixel against an intensity threshold to create a threshold image (FIG. 14C). The threshold image was used to establish a variable scan speed map, where dark and light regions in the threshold image correspond to faster and slower scan speeds, respectively. From the threshold image of FIG. 14C, a corrected threshold image was obtained, which is shown in FIG. 14D. The corrected threshold image attempts to consider real-world properties and limitations of galvanometer mirrors, notably by imposing the condition mentioned above that a minimum scan path distance should exist between two ROIs for the space therebetween to be considered a RONI and be scanned at a faster scan speed. As in FIG. 14C, the corrected threshold image of FIG. 14D can be used to establish a variable scan speed map, where dark and light regions in the corrected threshold image correspond to faster and slower scan speeds, respectively. The image of FIG. 14B was obtained using the scan speed map of FIG. 14D in 3.9 seconds, which is a 52% decrease in scan time compared to the time of 8.19 seconds it would take to acquire the entire image at the slower scan speed.

Referring to FIGS. 15A to 15D, some capabilities of the present techniques were also studied using resolution targets. FIGS. 15A and 15B are two images of a same sample acquired using different embodiments of the present techniques. FIGS. 15C and 15D are the scan speed maps used to acquire the images in FIGS. 15A and 15B, respectively, where dark and light regions correspond to faster and slower scan speeds, respectively. In both cases, the ratio of the faster scan speed to the slower scan speed is equal to four, but the scan speeds are globally higher in FIG. 15C than in FIG. 15D. Using these scan speed maps, the images of FIGS. 15A and 15B were acquired in 4.2 and 9.3 seconds, respectively, which represent decreases of 34% and 45% in scan times compared to the times required to acquire the same images using slower scan speeds only. It should be noted that the scan speed maps are not identical in FIGS. 15C and 15D, as the galvanometric response times are finite; and as scans are performed at faster speeds (FIG. 15C), fewer RONI sections are large enough for an acceleration and deceleration to occur within them, and they are therefore ignored, resulting in a larger proportion of the image being acquired at the slower scan speed in FIG. 15A than in FIG. 15B. It should also be noted that sparser images or images acquired using higher performance galvanometer mirrors can potentially yield even greater reductions in image acquisition time.

According to another aspect, there is provided a non-transitory computer readable storage medium or memory storing a computer program or executable instructions thereon that, when executed by a computer or processor, can perform various steps of the methods disclosed herein, for example determining a variable scan speed profile of a scan for acquiring a current scan line of an image of an object, for example an optical section of a sample.

In the present description, the terms "computer readable storage medium" and "computer readable memory" are intended to refer to a non-transitory and tangible computer product that can store and communicate executable instructions for the implementation of various steps of the method disclosed herein. The computer readable memory can be any computer data storage device or assembly of such devices, including random-access memory (RAM), dynamic RAM, read-only memory (ROM), magnetic storage devices such as hard disk drives, solid state drives, floppy disks and magnetic tape, optical storage devices such as compact discs (CDs or CDROMs), digital video discs (DVD) and Blu-Ray™ discs; flash drive memory, and/or other non-transitory memory technologies. A plurality of such storage devices may be provided, as can be understood by those skilled in the art. The computer readable memory may be associated with, coupled to, or included in a computer or processor configured to execute instructions contained in a computer program stored in the computer readable memory and relating to various functions associated with the computer.

In some implementations, the computer program stored in the computer readable storage medium can instruct a processor to perform the following steps: receiving at least one previously acquired predictive scan line, each of which provided as a series of pixel values as a function of position along the previously acquired predictive scan line; determining positions of one or more predicted regions of interest along the current scan line based on the pixel values of the at least one previously acquired predictive scan line; and determining the variable scan speed profile from the determined positions of the one or more predicted regions of interest, where the variable scan speed profile includes at least one slower speed component along segments of the scan corresponding to the positions of the one or more predicted regions of interest and at least one faster speed component along other segments of the scan.

In some implementations, the step of determining the positions of the one or more predicted regions of interest can include, for each previously acquired predictive scan line, steps of comparing the pixel values against one or more threshold criteria; and identifying, for each previously acquired predictive scan line, the positions of the one or more predicted regions of interest of the current scan line based on the positions of those pixel values that fulfill the one or more threshold criteria. As mentioned above, the one or more threshold criteria can include at least one of a presence-absence threshold criterion that the pixel values exceed a presence intensity threshold and a saturation threshold criterion that the pixel values remain below a saturation intensity threshold.

In some implementations, the at least one previously acquired predictive scan line includes multiple spatially registered predictive scan lines acquired using multiple detection channels, one of the predictive scan lines belonging to the image containing the current scan line. In such implementations, the step of determining the positions of the one or more predicted regions of interest along the current scan line can include a step of identifying a potential region of interest as one of the one or more regions of interest if a specified condition is met for at least one of the multiple spatially registered predictive scan lines.

In some implementations, the computer executable instructions can further cause the processor to control a scanner assembly to scan, in accordance with the variable scan speed profile, an illumination beam along a portion of the object corresponding to the current scan line.

In other implementations, the computer executable instructions stored in the computer readable storage medium can cause a processor to perform the following steps: receiving pixel data of a scan line currently being acquired at a scan speed; monitoring an absence or an end of a region of interest for upcoming pixels in the currently acquired scan line based on absence- or end-predictive variations in image signal intensity and, upon detection of such an absence or end, controlling a scanner assembly to set the scan speed at which the scan line is being acquired to a faster scan speed; monitoring an onset of a region of interest for upcoming pixels of the currently acquired scan line based on onset-predictive variations in image signal intensity and, upon detection of such an onset, controlling the scanner assembly to set the scan speed at which the scan line is being acquired to a slower scan speed; and repeating the monitoring steps until the end of the scan line is reached.

Of course, numerous modifications could be made to the embodiments described above without departing from the scope of the appended claims.

The invention claimed is:

1. A method for obtaining an image of an object, the image comprising a plurality of scan lines to be acquired, the method comprising, for a current one of the scan lines to be acquired:
   determining positions of one or more predicted regions of interest along the current scan line based on at least one previously acquired predictive scan line; and
   acquiring the current scan line along a scan path in accordance with a variable scan speed profile comprising at least one slower speed component along segments of the scan path corresponding to the positions of the one or more predicted regions of interest and at least one faster speed component along other segments of the scan path.

2. The method of claim 1, wherein the at least one previously acquired predictive scan line comprises at least one of the scan lines of the image of the object acquired before the current scan line.

3. The method of claim 2, wherein the at least one of the scan lines of the image acquired before the current scan line comprises the scan line acquired immediately before the current scan line.

4. The method of claim 2, wherein the at least one of the scan lines of the image acquired before the current scan line comprises multiple scan lines acquired successively before the current scan line.

5. The method of claim 1, wherein the at least one previously acquired predictive scan line comprises a flyback scan line acquired between the current scan line and the scan line of the image acquired immediately before the current scan line.

6. The method of claim 1, wherein the at least one previously acquired predictive scan line belongs to one or more images different from the image containing the current scan line.

7. The method of claim 6, wherein the image containing the current scan line and the one or more images containing the at least one previously acquired predictive scan line are acquired using distinct detection channels and a single illumination source.

8. The method of claim 6, wherein the image containing the current scan line and the one or more images containing the at least one previously acquired predictive scan line are acquired using distinct detection channels and distinct illumination sources.

9. The method of claim 6, wherein the image containing the current scan line and the one or more images containing the at least one previously acquired predictive scan line are acquired concurrently.

10. The method of claim 1, wherein the at least one previously acquired predictive scan line comprises multiple spatially registered predictive scan lines.

11. The method of claim 10, wherein determining the positions of the one or more predicted regions of interest along the current scan line comprises identifying a potential region of interest as one of the one or more predicted regions of interest if a specified condition is met for at least one of the multiple spatially registered predictive scan lines.

12. The method of claim 1, wherein determining the positions of the one or more predicted regions of interest comprises:
   receiving each previously acquired predictive scan line as a series of pixel values as a function of position along the previously acquired predictive scan line;
   comparing, for each previously acquired predictive scan line, the pixel values against one or more threshold criteria; and identifying the positions of the one or more predicted regions of interest of the current scan line based on the positions of those pixel values that meet the one or more threshold criteria.

13. The method of claim 12, wherein the one or more threshold criteria comprise at least one of a presence-absence threshold criterion that the pixel values exceed a presence intensity threshold and a saturation threshold criterion that the pixel values remain below a saturation intensity threshold.

14. The method of claim 1, wherein determining the positions of the one or more predicted regions of interest further comprises, prior to receiving each previously acquired predictive scan line, acquiring each previously acquired predictive scan line.

15. The method of claim 1, wherein acquiring the current scan line comprises:
   scanning an illumination beam over a portion of the object corresponding to the current scan line in accordance with the variable scan speed profile;
   detecting an object signal emanating from the scanned portion of the object; and
   generating the current scan line from the detected object signal.

16. The method of claim 1, wherein the at least one slower speed component consists of a single slower speed component with a slower nominal speed and the at least one faster speed component consists of a single faster speed component with a faster nominal speed.

17. The method of claim 16, wherein a ratio of the faster nominal speed to the slower nominal speed ranges between two and ten.

18. A non-transitory computer readable storage medium storing computer executable instructions for determining a variable scan speed profile of a scan for acquiring a current scan line of an image of an object, the computer executable instructions, when executed by a processor, cause the processor to perform the following steps:
   receiving at least one previously acquired predictive scan line, each of which provided as a series of pixel values as a function of position along the previously acquired predictive scan line;
   determining positions of one or more predicted regions of interest along the current scan line based on the pixel values of the at least one previously acquired predictive scan line; and
   determining the variable scan speed profile from the determined positions of the one or more predicted regions of interest, the variable scan speed profile comprising at least one slower speed component along segments of the scan corresponding to the positions of the one or more predicted regions of interest and at least one faster speed component along other segments of the scan.

19. The non-transitory computer readable storage medium of claim 18, wherein determining the positions of the one or more predicted regions of interest comprises:
   comparing, for each previously acquired predictive scan line, the pixel values against one or more threshold criteria; and
   identifying the positions of the one or more predicted regions of interest of the current scan line based on the positions of those pixel values that fulfill the one or more threshold criteria.

20. The non-transitory computer readable storage medium of claim 19, wherein the one or more threshold criteria comprise at least one of a presence-absence threshold criterion that the pixel values exceed a presence intensity threshold and a saturation threshold criterion that the pixel values remain below a saturation intensity threshold.

21. The non-transitory computer readable storage medium of claim 18, wherein the at least one previously acquired predictive scan line comprises multiple spatially registered predictive scan lines acquired using multiple detection channels, and determining the positions of the one or more predicted regions of interest along the current scan line comprises identifying a potential region of interest as one of the one or more regions of interest if a specified condition is met for at least one of the multiple spatially registered predictive scan lines.

22. The non-transitory computer readable storage medium of claim 18, wherein the computer executable instructions further cause the processor to control a scanner assembly to scan, in accordance with the variable scan speed profile, an illumination beam along a portion of the object corresponding to the current scan line.

23. An imaging system for obtaining an image of an object, the image comprising a plurality of scan lines to be acquired, the imaging system comprising:
   an illumination assembly generating an illumination beam;
   a scanner assembly scanning the illumination beam along a scan path across a portion of the object;
   a detector assembly detecting an object signal emanating from the scanned portion of the object and generating, from the detected object signal, a current one of the scan lines; and
   a processor configured to determine positions of one or more predicted regions of interest along the current scan line based on at least one previously acquired predictive scan line, and to control the scanner assembly to scan the illumination beam over the portion of the object corresponding to the current scan line in accordance with a variable scan speed profile comprising at least one slower speed component along segments of the scan path corresponding to the positions of the one or more predicted regions of interest and at least one faster speed component along other segments of the scan path.

24. The imaging system of claim 23, wherein the processor comprises a field-programmable gate array.

* * * * *